(12) United States Patent
Alessandrino

(10) Patent No.: US 11,696,972 B2
(45) Date of Patent: Jul. 11, 2023

(54) PROCESS FOR THE PRODUCTION OF A HYBRID STRUCTURE CONSISTING OF COUPLED SILK FIBROIN MICROFIBERS AND NANOFIBERS, HYBRID STRUCTURE THUS OBTAINED AND ITS USE AS IMPLANTABLE MEDICAL DEVICE

(71) Applicant: SILK BIOMATERIALS S.R.L., Lomazzo (IT)

(72) Inventor: Antonio Alessandrino, Como (IT)

(73) Assignee: SILK BIOMATERIALS S.R.L., Lomazzo (IT)

( * ) Notice: Subject to any disclaimer, the term of this patent is extended or adjusted under 35 U.S.C. 154(b) by 534 days.

(21) Appl. No.: 16/941,273

(22) Filed: Jul. 28, 2020

(65) Prior Publication Data

US 2020/0353125 A1 Nov. 12, 2020

Related U.S. Application Data

(62) Division of application No. 15/522,397, filed as application No. PCT/IB2015/058262 on Oct. 27, 2015, now Pat. No. 10,758,641.

(30) Foreign Application Priority Data

Oct. 27, 2014 (IT) .......................... MI2014A001841

(51) Int. Cl.
*A61L 27/36* (2006.01)
*A61F 2/02* (2006.01)
*A61L 27/54* (2006.01)
*A61L 27/22* (2006.01)

(52) U.S. Cl.
CPC ............ *A61L 27/3604* (2013.01); *A61F 2/02* (2013.01); *A61L 27/227* (2013.01); *A61L 27/54* (2013.01); *A61L 2300/406* (2013.01); *A61L 2300/414* (2013.01); *A61L 2400/12* (2013.01)

(58) Field of Classification Search
CPC ............... A61L 27/227; A61L 27/3604; A61L 27/3662; A61L 2400/12
See application file for complete search history.

(56) References Cited

U.S. PATENT DOCUMENTS 8,202,379 B1 6/2012 Delong et al.
10,080,644 B2 9/2018 Goh et al.

FOREIGN PATENT DOCUMENTS

CN 101879330 A 11/2010
DE 1436311 A1 7/1969

OTHER PUBLICATIONS

International Preliminary Report on Patentability for corresponding Application No. PCTIIB2015/058262 (dated Dec. 12, 2016).
(Continued)

*Primary Examiner* — William H Matthews
(74) *Attorney, Agent, or Firm* — Troutman Pepper Hamilton Sanders LLP (Rochester)

(57) ABSTRACT

A method is described for the production of hybrid structures formed by the coupling of nanofibrous parts and microfibrous parts made with silk fibroin, possibly hierarchically organized into complex structures comprising more than two of said parts; these hybrid structures are used as implantable biomedical devices with tailored biological, geometrical and structural features, such that they can be adapted to different application requirements in the field of regenerative medicine.

12 Claims, 11 Drawing Sheets

(56) References Cited

OTHER PUBLICATIONS

International Search Report and Written Opinion for corresponding Application No. PCT/IB2015/058262 (dated Feb. 12, 2016).
Navone et al., "Decellularized Silk Fibroin Scaffold Primed With Adipose Mesenchymal Stromal Cells Improves Wound Healing in Diabetic Mice," Stem Cell Res Ther 5(1):7 (2014).
Dal Pra et al., "De Novo Engineering of Reticular Connective Tissue In Vivo by Silk Fibroin Nonwoven Materials," Biomaterials 26(14):1987-99 (2005).
Cattaneo et al., "In Vivo Regeneration of Elastic Lamina on Fibroin Biodegradable Vascular Scaffold," Int J Artif Organs 36(3):166-74 (2013).

PROCESS FOR THE PRODUCTION OF A HYBRID STRUCTURE CONSISTING OF COUPLED SILK FIBROIN MICROFIBERS AND NANOFIBERS, HYBRID STRUCTURE THUS OBTAINED AND ITS USE AS IMPLANTABLE MEDICAL DEVICE

This application is a division of U.S. patent application Ser. No. 15/522,397, filed on 27 Apr. 2017, now U.S. Pat. No. 10,758,641, issued on 1 Sep. 2020, which is a national stage application under 35 U.S.C. § 371 of PCT Application No. PCT/IB2015/058262, filed 27 Oct. 2015, which claims priority of Italy Application No. MI2014A001841, filed 27 Oct. 2014, which are hereby incorporated by reference in their entirety.

FIELD OF THE INVENTION

The present invention relates to a process for the production of a hybrid structure consisting of mutually coupled fibroin microfibers and nanofibers, possibly hierarchically organized into complex structures comprising several primary structures obtained from the coupling of nano- and microfibrous fibroin; the invention also relates to the hybrid structure obtained by the process, and its use as an implantable medical device for use in a wide range of applications in the field of tissue engineering and regenerative medicine.

BACKGROUND ART

In modern surgery, scaffolds are increasingly used, which are implantable devices that have the function of temporarily compensating the impaired functionality of body parts and tissues, and which are then colonized by the natural cellular regrowth of the damaged part or tissue to achieve the regeneration of the same.

The materials for producing the scaffolds can be very different, depending on the intended application. For example, inorganic scaffolds consisting of mixtures of hydroxyapatite and β-tricalcium phosphate are typically used for the temporary replacement and regrowth of bone tissue. However, polymeric scaffolds are far more common, preferably based on biodegradable and biocompatible biopolymers or synthetic polymers, intended to temporarily replace non-rigid tissues.

A polymeric scaffold must possess a series of surface and bulk properties optimized for the function to be carried out in vivo. Among the properties of interest we may consider the morphological characteristics at a nano, micro and macroscopic level; the physical-mechanical properties and performance (ideally, these should be as close as possible to the in vivo characteristics and performance of the tissues to be regenerated); and the chemical and biological properties, with particular reference to biocompatibility (i.e. the ability of supporting adhesion and cell growth, not causing inflammatory and/or immunogenic reactions, not releasing hazardous substances, etc.) and to biodegradability or bioresorbability (which must be commensurate with the residence time of the device in vivo, which in turn depends on the reconstruction rate of the tissue to be repaired). Other properties of interest can be porosity, permeability to fluids, ability to uptake, retain and then release, when required, active agents, growth factors or drugs, etc. to the implantation site.

A particularly promising natural polymer for use in the production of scaffolds is fibroin, a silk protein produced in nature by Lepidoptera (domestic species: *Bombyx mori*; wild species: *Antheraea pernyi*, *Philosamia ricini*, etc.), other insects and arachnids. Fibroin can also be produced by recombinant DNA techniques. Fibroin is obtained from natural silk with the so-called "scouring" treatment, which consists in the removal of the sericin layer covering the fibroin; this treatment is generally carried out through a water bath optionally added with alkalis (soap), acids or enzymes, at temperatures between about 60 and 120° C., if necessary by operating in an autoclave. The fibroin thus obtained is in the form of microfibers having an average diameter of 12-14 μm, with an ultimate strength of about 600 MPa and elongation at break values of 25-30% (values referred to the microfiber of *B. mori*). Two- or three-dimensional structures (threads, yarns, woven fabrics, knitted fabrics, nonwoven fabrics, nets, braids, cords, etc.) can be produced with these microfibers, making use of technologies developed for silk applications in the textile field and which thus fall within the ordinary knowledge of the man skilled in the art.

The interest towards fibroin is mainly due to its proven biocompatibility, which is expressed through the ability of supporting the growth and proliferation of various cell types, the lack of immunogenic and inflammatory reactions, and the marked angiogenic properties, particularly useful in the case of the repair/regeneration of living tissues. In addition, the physical-mechanical characteristics mentioned above allow producing scaffolds with mechanical properties suitable for the purpose (in particular, high resistance to tensile, bending, compression stress; good elasticity; resilience, etc.); finally, the scaffolds made of fibroin have biodegradability characteristics in the medium-long term in vivo (from a few months to 1-2 years, depending on the characteristics of the biological environment of the implantation site), optimal for applications in which the scaffold must ensure mechanical support for prolonged times.

Thanks to these properties, fibroin has already been proposed in the art for the production of scaffolds.

The coupling of polymers in the form of fibers through partial dissolution and subsequent re-deposit of polymer on the fibers is known for example from patent application DE 1436311 A1.

U.S. Pat. No. 8,202,379 B1 describes the coupling of fibers of natural or synthetic polymers by treatment of the same with mixtures containing an ionic liquid and a second liquid compound, generally water, an alcohol or a ketone.

These documents only describe the coupling of fibers homogeneous in size and chemical, physical and mechanical properties (as derived from the same production and/or working process).

Patent applications WO 03/043486 A2, EP 2210971 A1 and WO 2011/031854 A1 describe fibroin structures intended for the reconstruction of ligaments (in particular the anterior cruciate ligament of the knee), consisting of a hierarchy of fibrous structures assembled at increasing levels up to reaching the dimensions and the mechanical performance required for the application.

Patent applications WO 2013/012635 A2, WO 2013/082093 A1 and WO 2012/111309 A1 describe instead devices based on native fibroin microfibers, having a net structure obtained by knitting, optimized for the reparative surgery of damaged tissues in the abdominal and pelvic areas, for plastic surgery of the breast, and for the realization of vascular prostheses, respectively.

These scaffolds are produced from fibroin microfibers (which as said have diameters of about 12-14 μm) through the use of textile technologies, in which the basic silk thread, consisting of at least 20 microfibers of fibroin, is generally assembled by doubling and twisting operations in hierarchically superior structures ("yarns") whose transverse dimensions may range from a tenth of a millimeter up to one millimeter or more. Although the textile structures thus produced usually have excellent characteristics of softness and smoothness and at a macroscopic level they adapt easily to the surface to which they adhere, at a microscopic level they can display stiffness areas such as to cause local irritation/inflammation reactions; furthermore, due to their high crystallinity and toughness, fibroin microfibers are able to exert friction forces of such magnitude as to abrade the surface of the tissue with which they come into contact; these problems can lead, in the worst cases, to the partial or total failure of the implant. Another drawback of fibroin microfiber scaffolds is that they display unfavorable surface/volume ratios, so that a total area suitable for autologous colonization involves a relatively high load of material to be placed in the implantation site, with the consequences of a potential overload of physiological and metabolic activity due to a local accumulation of degradation products to be disposed of by the organism. Finally, the natural degradation times of the fibroin microfibers in some cases may be too long compared to the rate of neo-tissue formation, and thus interfere with its growth.

In order to obviate these drawbacks, it has been proposed the use of fibroin in the form of nanofibers, that is, having a diameter less than one micron and typically from a few tens up to a few hundred nanometers.

These nanofibers can be produced by known processes, in which the native fibroin is first solubilized in a suitable solvent, and then regenerated with processes such as force-spinning or electrospinning. In these processes, the solution of fibroin is passed through a capillary tube, called a spinneret, giving rise to a liquid filament of nanoscopic dimensions, which is accelerated towards a collector; in the case of force-spinning, the acceleration is caused by the centrifugal force (due to the rotation of the spinneret at a speed of several thousand rpm), while in the case of electrospinning, it is caused by a potential difference between the nozzle of the spinneret and a manifold, which loads the liquid thus causing the production of a jet of solution; thanks to the viscoelastic properties of the polymer, the jet undergoes a drawing process which, accompanied by the simultaneous evaporation of the solvent, leads to the production of the nanofiber which accumulates on the collector.

Recent studies have demonstrated the excellent properties of the scaffolds made with fibroin nanofibers.

The article "In vivo regeneration of elastic lamina on fibroin biodegradable vascular scaffold", I. Cattaneo et al., Int. J. Artif. Organs 36 (2013) 166, shows that a tubular scaffold of electrospun fibroin, implanted in the abdominal portion of the aorta of the rat, allows the formation of a vascular tissue totally similar to the native one from the morphological and functional point of view. The article "Decellularized silk fibroin scaffold primed with adipose mesenchymal stromal cells improves wound healing in diabetic mice", S. E. Navone et al., Stem Cell Research & Therapy, 5 (2014) 7, shows the effectiveness of electrospun fibroin patches, pre-activated by contact with mesenchymal cells of the adipose tissue, in inducing wound healing in diabetic mice through biological mechanisms involving the direct stimulation of angiogenic processes by the material.

Scaffolds have also been described made by coupling of fibroin microfibers and nanofibers.

Patent application CN 101879330 A describes a device, proposed as a vascular prosthesis and/or a guide for the regeneration of nerves, having a three-layers tubular structure, wherein the inner layer is a porous deposit made from regenerated fibroin, the intermediate layer is a tubular structure of woven microfibers of fibroin in the form of a net, and the outer layer consists of a nanofibrous fibroin structure produced by electrospinning. The production process of the device described in this document is complex. The inner layer is initially produced in tubular shape with standard weaving methods, the layer thus obtained is immersed in a solution of fibroin and the resulting intermediate product is dried at 40-60° C. This first intermediate product is fitted onto a collector pin for electrospinning, and a layer of nano-microfibrous fibroin is deposited on the outer surface of said first intermediate product mentioned above by means of this technique; the composite thus obtained is then immersed in methanol or ethanol for 1-4 hours. Finally, this first composite is introduced into a mold and the porous layer is produced on its inner tubular surface by deposit from a fibroin solution; the porosity of the innermost layer is obtained by a treatment at temperatures between −80° C. and −10° C. The three layers of this composite are bonded together by means of fibroin films that are formed on the surface of the same during the immersions in solvents or in fibroin solutions. The fibroin films produced according to the process of this document, however, once dried and crystallized are extremely fragile, such as to fracture immediately as they are urged by tensile, bending, compression, etc., mechanical stress; this can lead to the creation of morphological and mechanical discontinuity between the different layers which can easily lead to a loss of the geometric and performance characteristics, such as the yielding and/or the collapse of the weaker layers from the mechanical point of view (in particular the nanofibrous ones).

Patent application CN 102499800 A describes a device which may find application as a stent or prosthesis for the repair of small blood vessels, also in this case consisting of a hybrid structure with three layers; the inner and the intermediate layer are made of nanofibrous structures obtained by electrospinning of a fibroin/polycaprolactone mixture, while the outer layer consists of a tubular structure of fibroin microfibers, produced with a braiding machine. The three layers, produced separately and fitted one on top of the other as sleeves, are held together by a series of annular stitches. This device partly has the same drawbacks as the former one; furthermore, the fact that the coupling is realized with stitches spaced apart from one another leaves a partial freedom of movement to the various components; in stressing working conditions from the mechanical and biological point of view, such as those that can occur in the progress of the implantation in vivo, this could create local stresses of such a magnitude as to interfere with the regenerative processes in progress, especially if the material is exposed to flows of physiological fluids.

The object of the present invention is to provide a hybrid composite material made of fibroin micro- and nanofibers which allows producing scaffolds for medical applications free from the drawbacks of the prior art.

SUMMARY OF THE INVENTION

This object is achieved with the present invention, which in a first aspect thereof relates to a process for the production of a hybrid structure made of microfibers and nanofibers of silk fibroin coupled to one another, which comprises the following steps:

a) preparation of one or more parts made of microfibrous fibroin;

b) preparation of one or more parts made of nanofibrous fibroin;

c) treatment of said one or more parts of nanofibrous fibroin and of said one or more parts of microfibrous fibroin, separately or after coupling, with a solvent for fibroin and/or with a solution comprising fibroin dissolved in a solvent;

c') if in step c) the nanofibrous and microfibrous parts have been treated separately with a solvent for fibroin and/or with a solution comprising fibroin dissolved in a solvent, coupling of said parts;

d) consolidation of the hybrid microfibrous/nanofibrous structure obtained in step c) or in step c') by thermal treatment at a temperature between 10° C. and 150° C., for a time between 1 minute and 24 hours;

e) removal of the solvent by washing with water or a water-alcohol mixture or by evaporation at temperatures between 10° C. and 100° C., possibly under vacuum, wherein the solvent used in step c) is selected from: formic acid, 1,1,1,3,3,3-hexafluoro-2-propanol, trifluoroacetic acid, hexafluoroacetone, N-methylmorpholine N-oxide, ionic liquids, calcium chloride-ethanol-water mixtures, calcium nitrate-methanol-water mixtures, aqueous solutions of lithium salts and mixtures among these solvents and/or with water.

The process of the invention may further comprise the following additional steps:

f) coupling of two or more micro/nanofibrous hybrid structures obtained according to steps a) to e) to form a superior hierarchical structure;

g) consolidation of the superior hierarchical structure thus obtained by repetition on the same of steps c) to e) mentioned above.

In a second aspect thereof, the invention relates to implantable medical devices that use the hybrid structures obtained with said process.

BRIEF DESCRIPTION OF THE FIGURES

The invention will now be described in detail hereinafter with reference to the accompanying drawings, in which.

DETAILED DESCRIPTION OF THE INVENTION

Figure 1:
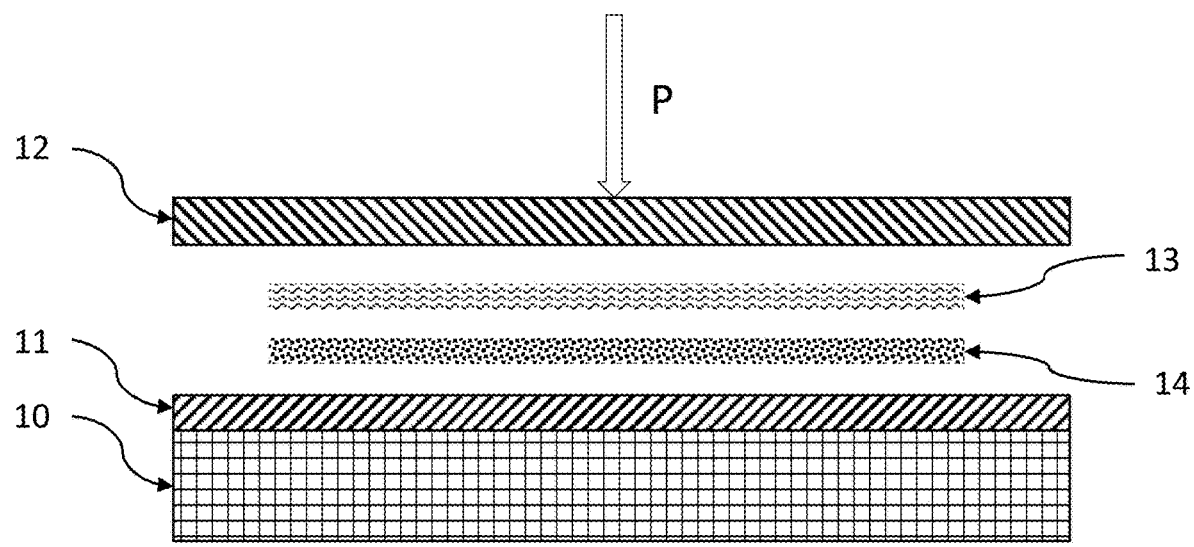
FIG. 1 schematically shows an apparatus for carrying out the operation of coupling nanofibrous and microfibrous parts according to the invention.

In the present description and in the following claims, the term "part" means a body formed from homogeneous fibers of fibroin, that is, only microfibers or only nanofibers, while the term "hybrid structure" means a body formed by coupling of at least one part formed from nanofibers and at least one part formed from microfibers.

The inventors have discovered that by combining fibroin nanofibers and microfibers according to the process described hereinafter it is possible to form hybrid structures provided with mechanical properties adapted for the production of implantable medical devices.

The nanofibers useful for the purposes of the invention have diameters between 20 nm and 1.5 µm, and preferably between 0.4 and 1 µm. Microfibers instead typically have diameters between about 10 and 15 µm; the microfibers may also be coupled into multifiber yarns, containing even up to 500 individual silk filaments. In the remainder of the text, the unit of measurement den is also used, typical of the textile technology, defined as weight in grams of 9000 meters of fiber or yarn.

In the first aspect thereof, the invention relates to the production process of micro/nanofibrous hybrid structures by coupling of one or more fibroin microfibrous parts and one or more fibroin nanofibrous parts.

Step a) of the process consists in the preparation of one or more microfibrous fibroin parts. The fibroin microfibrous part confers the shape and mechanical strength to the final medical device; as first step of the process it is therefore necessary to prepare a fibroin microfibrous part having shape and dimensions essentially corresponding to those of the desired device. Microfibrous fibroin is used as starting material for the production of this part, in the form of a silk yarn having a count of between 10 den and 400 den, and preferably between 15 den and 100 den. The silk yarn can be used after scouring or it can be used raw and scoured after the production of the part. The microfibrous fibroin can be added with bioactive agents including growth factors, drugs, cells, antibiotics, antiviral agents, enzymes, vitamins, etc., for example by means of chemical and/or enzymatic reactions. This addition may be made prior to step a), during any of steps c) to g), or later on. This part may be formed by one or more elements obtained by any of the techniques known in the textile industry, such as weft-warp weaving (obtaining an orthogonal fabric), production techniques of nonwoven fabric, knitting, braiding, or the technique known as "filament winding", which consists in the winding of yarns, according to variable interweaving patterns, around a rotating spindle, which leads to the obtaining of hollow cylindrical structures.

Step b) of the process consists in the preparation of one or more nanofibrous fibroin parts. Nanofibrous fibroin parts useful for the purposes of the invention can be obtained through force-spinning, or preferably through electrospinning, of a fibroin solution.

The starting solution is prepared by dissolving fibroin in a solvent selected from formic acid, 1,1,1,3,3,3-hexafluoro-2-propanol, trifluoroacetic acid, or ionic liquids such as 1-ethyl-3-methylimidazolium chloride, 1-butyl-3-methylimidazolium chloride, 1-ethyl-3-methylimidazolium acetate, 1-ethyl-3-methylimidazolium glycine, 1-allyl-3-methylimidazolium chloride, 1-butyl-2,3-dimethylimidazolium chloride, 1-butyl-3-methylimidazolium bromide and mixtures among these solvents and/or with water; the preferred ionic liquids for the purposes of the invention are 1-ethyl-3-methylimidazolium chloride, 1-butyl-3-methylimidazolium chloride, 1-ethyl-3-methylimidazolium acetate and 1-ethyl-3-methylimidazolium glycine.

The starting solution has a fibroin concentration of between 1% w/v and 30% w/v, preferably between 6% w/v and 10% w/v, in formic acid; or alternatively, a fibroin concentration of between 5% w/v and 40% w/v, preferably between 10% w/v and 30% w/v, in the other solvents indicated; the weight/volume (% w/v) percentage concentration indicates the grams of fibroin dissolved in 100 mL of solution.

The preferred method of production of the nanofibrous fibroin part is electrospinning, the general execution methods of which are known to the man skilled in the art: in order to obtain a nanofibrous fibroin suitable for the purposes of the invention, the solution is electrospun with a potential difference between the nozzle of the spinneret and the collector between 5 kV and 100 kV, preferably between 15 kV and 35 kV, with a distance between said nozzle and collector between 5 cm and 60 cm, preferably between 10 cm and 20 cm. The nozzle of the spinneret can have diameters of between 0.01 mm and 10 mm, preferably between 0.1 mm and 1 mm.

Both in the case of force-spinning and of electrospinning, the starting solution may be added with bioactive agents including growth factors, drugs, cells, antibiotics, antiviral agents, enzymes, vitamins, etc., which are thus integrated in the medical device and can then be released from the same at the implantation site, in order to promote the regenerative processes of the body area said device is intended for. The nanofibrous fibroin can be added with bioactive agents including growth factors, drugs, cells, antibiotics, antiviral agents, enzymes, vitamins, etc., for example by means of chemical and/or enzymatic reactions. This addition may be made during any of steps c) to g), or later on.

The previous steps have been named a) and b) only for the purposes of clarity of illustration, but this does not imply a temporal order of execution; nano and microfibrous parts are produced separately, and the two steps may be carried out in any sequence.

After their preparation, in step c) of the process, the parts of microfibrous and nanofibrous fibroin are treated with a solvent or a solution containing additional fibroin. In this step, a surface fraction of the fibers passes to the gel phase, forming a film around the present fibers. The treatment with said solvent or solution can take place on said separate parts, or after having put them in contact with one another.

In the case of treatment with solvent alone, this is selected from: an ionic liquid that can be 1-ethyl-3-methylimidazolium chloride, 1-butyl-3-methylimidazolium chloride, 1-ethyl-3-methylimidazolium acetate, 1-ethyl-3-methylimidazolium glycine, 1-allyl-3-methylimidazolium chloride, 1-butyl-2,3-dimethylimidazolium chloride, 1-butyl-3-methylimidazolium bromide or mixtures thereof, pure or in mixture with water; formic acid; trifluoroacetic acid; 1,1,1,3,3,3-hexafluoro-2-propanol; hexafluoroacetone; calcium chloride-ethanol-water mixtures; calcium nitrate-methanol-water mixtures; N-methylmorpholine N-oxide; or aqueous solutions of lithium salts (lithium bromide, lithium thiocyanate). The preferred solvents for this treatment are 1-ethyl-3-methylimidazolium chloride, 1-butyl-3-methylimidazolium chloride, 1-ethyl-3-methylimidazolium acetate, 1-ethyl-3-methylimidazolium acetate or 1-ethyl-3-methylimidazolium glycine, pure or mixtures thereof with water with a water content of between 5% w/w and 50% w/w and preferably between 10% w/w and 25% w/w; another preferred solvent for the purposes of the invention is formic acid.

The exposure to the solvent of the nanofibrous and microfibrous fibroin parts (either separate or already in contact with one another) can take place according to different methods, such as for example:

immersion in the solvent, for a time between 1 second and 240 minutes, preferably between 30 seconds and 30 minutes;

deposition of the solvent by pouring, coating, atomizing, electrospray or electrospinning, in an amount between 0.001 mL/cm$^2$ and 0.5 mL/cm$^2$, preferably between 0.01 mL/cm$^2$ and 0.1 mL/cm$^2$; these amounts are referred to the apparent surface of the parts, i.e. those deduced from the simple multiplication of the length and width of the parts themselves (the contribution of the height to the surface of the part is in general negligible), and not to the overall surface of the individual fibers;

exposure to the vapors of the solvent, for a time between 1 second and 120 minutes, preferably between 30 seconds and 30 minutes.

The temperature at which the contact between the microfibers and the solvent is made is variable between 40 and 80° C., preferably between 50 and 70° C.; it is also possible to operate at temperatures lower than 40° C., but in this case the process execution time becomes very long and not suitable for an industrial production. For the nanofibers, the temperature at which contact with the solvent is made is variable between room temperature and 70° C., preferably between 40 and 60° C.

In the case of separate treatment of the two parts prior to their coupling, it is possible to treat one of the two with solvent alone, and the other with a solution of fibroin in a solvent (not necessarily the same as that of the treatment with solvent alone).

It is also possible to treat one or both parts in succession with the solvent alone to cause an initial gelling of the fibers, and then with a solution of fibroin to impart an additional aliquot of dissolved polymer and facilitate the subsequent coupling of the parts.

For an optimal execution of the process of the invention, the contact time between fibers and solvent should be reduced, in the ranges mentioned above, with increasing temperature and with decreasing dimensions of the yarns or dimensions of the parts to be treated. For example, for the same thickness of the microfibers, suitable contact times with the solvent will be between about 30 seconds and 3 minutes at temperatures between 70 and 80° C., and between about 15 minutes and one hour for temperatures between 40 and 50° C. As regards the nanofibers, these contact times range between 30 seconds and one minute at 70° C., and between about 5 and 30 minutes at temperatures between 40 and 50° C.

The contact times, with the same temperature, also vary depending on the apparent density of the part, i.e. the amount of fibers per unit of volume of the same, especially in the case of parts made of microfibers; still remaining in the general ranges mentioned above, the suitable contact time for a fabric decreases, for example passing from crêpe to twill, from twill to organdie and from organdie to nonwoven fabric.

Taking into account these general guidelines, the man skilled in the art is able to choose the optimal operating conditions suitable for obtaining the effective coupling of the available microfiber and nanofiber parts.

In the case of treatment with a fibroin solution, the solution is produced with the same solvents mentioned above for treatment with the solvent alone. Preferably, the solution is based on 1-ethyl-3-methylimidazolium chloride, 1-butyl-3-methylimidazolium chloride, 1-ethyl-3-methylimidazolium acetate or 1-ethyl-3-methylimidazolium glycine, pure or mixed with water (water content between 5% w/w and 50% w/w, preferably between 10% w/w and 25% w/w), with a concentration of fibroin between 5% w/v and 40% w/v, preferably between 10% w/v and 30% w/v; or based on formic acid with a concentration of fibroin between 1% w/v and 30% w/v, preferably between 6% w/v and 10% w/v.

The contact between the fibroin solution and the nanofibrous and microfibrous fibroin parts can occur through immersion in solvent or deposition of the same on said parts (already in contact with one another or still separate), with the same methods, timing and quantity amounts reported above in case of treatment with solvent alone.

If said parts were not already in contact with one another before said treatments with solvent or solution, these are put in contact with one another in step c'), obtaining a micro/nanofibrous hybrid structure.

In the case of planar geometry devices, the nanofibrous and microfibrous parts are stacked (placed) on top of one another according to desired number and sequences. In the case of tubular medical devices, the nanofibrous and microfibrous parts are "fitted" on top of one another according to desired number and sequences. In the case of three-dimensional hybrid structures other than tubular, the nanofibrous and microfibrous parts are made to adhere to one another according to desired number and sequences.

In steps c) and c') it is possible to add the hybrid structure being formed with bioactive agents, including growth factors, drugs, cells, antibiotics, antiviral agents, enzymes, vitamins, etc., dispersing such bioactive agents in the solvents and/or solutions used. In this way, the bioactive agents come into contact with the component parts of the hybrid structure and can be incorporated therein and therefore in the implantable medical devices in which this is used.

In step d) of the process, the hybrid structure thus obtained is then subjected to heat treatment to strengthen the coupling of the two or more fibroin parts, of which at least one of nanofibrous fibroin and at least one of microfibrous fibroin. This treatment is carried out on the hybrid structure still impregnated with solvent, at a temperature between 10° C. and 150° C.; preferably, the treatment temperature is between 80° C. and 120° C. when an ionic liquid is used in the previous step, and between 20° C. and 50° C. when formic acid or other solvents are used in the previous step. The duration of treatment is between 1 minute and 24 hours.

Preferably, during step d), the set of parts to be coupled is subjected to compression, typically at values between 0.5 and 5 kg/cm$^2$, preferably between 0.1 and 1 kg/cm$^2$, to increase the efficiency of the distribution process onto both types of fibers of the gelified fibroin formed in step c).

This operation can be carried out for example by means of an apparatus such as that shown in FIG. 1. The apparatus includes a heating element 10 at the bottom, upon which a plate 11 rests; in its upper part, the apparatus includes a second plate 12. The two plates must be made of rigid, thermally conductive and non-stick material. The heating element must allow a fine control of the temperature, in the range of treatment temperatures mentioned above, with an accuracy of ±0.5° C., better if ±0.1° C., in order to allow the management of the gelling process with the necessary accuracy. According to the preferred operating method described above, a light pressure (shown in the figure by the arrow directed downwards and by the indication "P") is applied on the top plate during the heating step using a weight and/or a closing system that brings the two plates close to each other so as not to leave any empty space between the fibroin parts, nor between said parts and the plates. Finally, the device is preferably locked in a heat-insulating chamber, accessible from the outside, in order to prevent heat losses that might impair the effectiveness of the gelling process. The optimal arrangement of the two parts of fibroin to be coupled is as shown in the figure, with the microfibrous part 14, less sensitive to the effects of heat combined with the ionic liquid, in contact with plate 11 adjacent to the heating element, while the nanofibrous part 13 is in contact with the top plate 12. This configuration (microfibrous part closer to the heating element and nanofibrous part farther therefrom) is preferable also in the case of hierarchically superior hybrid structures obtained according to steps f) and g) of the process, when allowed by the stacking order of the parts.

In the case of tubular parts, the coupling is carried out for example with an apparatus consisting of a cylinder that may be solid or hollow, made of rigid, thermally conductive and non-stick material and with a diameter slightly greater than the diameter of the parts to be coupled (with a difference in diameter preferably between 0.05 mm and 3 mm). The spindle must be connected to a system suitable for adjusting the temperature thereof between 10° C. and 150° C. and it may be contained in a heat-insulating chamber; this chamber may be thermostatically controlled and allow temperature control in the same range. In this operating mode, one of the parts is fitted on the spindle and then the other part is fit onto the first one, in both cases taking advantage of the elasticity of the fibroin parts. The difference in size between the spindle and the parts generates a radial pressure of the outermost parts on the innermost parts, promoting the adhesion and the coupling of the same parts. The preferred configuration in this operating mode is determined by the final objective of the produced device; therefore, by way of example, for the manufacture of medical devices for the repair/regeneration of blood vessels, the nanofibrous part will be mounted in contact with the spindle while the microfibrous part will be fitted on the nanofibrous part.

In step e) of the process, the solvent is removed by washing with water or a water-alcohol mixture, or by evaporation. Washing is carried out at a temperature between 10° C. and 100° C., preferably between 20° C. and 50° C., for a time between 2 minutes and 180 minutes, preferably between 10 minutes and 60 minutes; the preferred alcohols in case of use of water-alcohol mixtures are methanol and ethanol, with water concentrations between 5% v/v and 50% v/v and preferably between 10% v/v and 30% v/v. If the solvent is removed by evaporation, this is carried out at a temperature between 10° C. and 100° C. possibly under vacuum, preferably between 15° C. and 55° C., for a time between 10 minutes and 168 hours and preferably between 30 minutes and 72 hours.

Steps c) and d) of the process lead to a partial surface solubilization/gelification of the fibrous material making up the adjacent parts. The next step e) of solvent removal causes the coagulation of the gelified fibroin fraction; the passage of fibroin from the gel state to the solid (coagulated) state that takes place in the contact areas between the structures leads to the formation of "junctions", union and fusion points between microfibers and nanofibers. This forms a hybrid structure consisting of microfibers and nanofibers welded together and constituting a single part.

Once a micro/nanofibrous hybrid structure has been produced as described above, this can be coupled to another or to several similar structures to form hierarchically organized complex structures, by carrying out the optional steps f) and g) mentioned above.

The second aspect of the invention relates to the implantable medical devices that use the hybrid structures obtained with the process described thus far.

The implantable medical devices of the invention are mainly used as scaffolds for repairing human and animal tissues and organs with regenerative medicine approach. Among the target tissues and organs we may mention, among the others, tissues of the peripheral nervous system (peripheral nerves), vascular system (veins, arteries, arteriovenous fistulas for vascular access), cardiovascular system (coronary arteries and the heart muscle), central nervous system (spinal cord), skin and its layers, containment and protection tissues of internal organs (dura mater, pericardium, pleura, peritoneum, . . . ), tissues of the musculoskeletal system (tendons, ligaments, muscles) and devices for the containment of hernias and prolapses.

The shape and size of the device depend on the target tissue or organ; below are listed the rough shapes and sizes of devices intended for some of the purposes mentioned above and achievable using the hybrid structures of the invention, but other possible uses (and the shapes and sizes of relevant devices) will be apparent to the man skilled in the art:
- tubular devices with inner diameter of between 2 mm and 8 mm and wall thickness of between 0.2 mm and 4 mm in the case of peripheral blood vessels;
- tubular devices with inner diameter of between 1 mm and 6 mm and wall thickness of between 0.2 mm and 1 mm in the case of peripheral nerves;
- solid cylindrical devices with outer diameter of between 2 mm and 15 mm in the case of tendons and ligaments;
- planar devices with thickness of between 0.1 mm and 5 mm in the case of the skin and its layers;
- planar devices with thickness of between 0.05 mm and 2 mm in the case of containment and protection tissues of internal organs such as dura mater, pericardium, pleura, peritoneum;
- planar devices with thickness of between 0.05 mm and 2 mm in the case of devices for the containment of hernias and prolapses.

The invention will be further illustrated by the following examples.

Example 1

This example describes the production of microfibrous fibroin filaments and of parts (fibers, fabrics) obtained from these filaments.

Cocoons of *B. mori* were subjected to spinning to produce a raw silk yarn. After doubling and twisting, the yarn was scoured with water under pressure at 120° C. for 30 min to remove the sericin. For the production of fabrics, the raw yarn was first woven in the desired weaves and the fabric thus obtained was then scoured at 95-98° C. for 1 hour, in the presence of surfactants to remove the sericin. To produce the non-woven fabric, the cocoons were cut and macerated to remove the sericin. The short fiber silk thus obtained (called "shappe") was subjected to carding. The veil of card was consolidated into non-woven by needling.

The following was produced with the thus obtained filaments:
- a scoured silk yarn (3 yarn weft; count 17.1×3 den);
- a scoured silk fabric having the following features: weave: crêpe; no. yarns/cm in warp: 58 (count: 15.3×3 den); no. yarns/cm in weft: 39 (count: 15.3×3 den); mass per unit area: 55 g/m$^2$; thickness 0.12 mm;
- a scoured silk fabric having the following features: weave: organdie; no. yarns/cm in warp: 53 (count: 20.7 den); no. yarns/cm in weft: 39 (count: 23.4 den); mass per unit area: 30 g/m$^2$; thickness 0.09 mm;
- a scoured silk fabric having the following features: weave: twill; no. yarns/cm in warp: 55 (count: 15.3×3 den); no. yarns/cm in weft: 43 (count: 15.3×4 den); mass per unit area: 60 g/m$^2$; thickness 0.09 mm;
- a non-woven fabric (TNT) of scoured silk, having the following features: fiber length: 20-27 mm; mass per unit area: 33 g/m$^2$.

These samples are used for the tests of the following examples.

Example 2

This example describes the production of nanofibrous fibroin parts.

Cocoons of *B. mori* were scoured with distilled water in autoclave at 120° C. for 30 min, to remove the sericin.

After thoroughly rinsing and drying at room temperature, 1 g of fibroin microfibers was dissolved in 10 mL of a saturated solution of LiBr (about 9.3 M) for 3 hours at 60° C. After dilution with an equal volume of distilled water, the fibroin solution was dialyzed for 3 days against distilled water to remove the salt. The resulting fibroin solution was diluted to 67 mL with water, resulting in a 1.5% w/v aqueous solution of fibroin. The solution, divided into 15 mL aliquots, is poured into molds with a diameter of 5 cm and allowed to evaporate at room temperature, obtaining fibroin films having an average thickness of 50 μm.

Just before the electrospinning process, 2 g of film are dissolved in 25 mL of formic acid at room temperature, obtaining a solution with a polymer concentration equal to 8% w/v.

For the production of nanofibrous fibroin parts, the fibroin solution in formic acid is loaded in a polypropylene syringe attached to a syringe pump (Graseby Medical, M S 2000) with a PTFE capillary tube. The electrospinning system consists of two high voltage power supplies (F.u.G. Elektronik GmbH, HCN 35-12500) capable of generating up to 25 kV. The positive pole is connected to the spinneret, consisting of a steel capillary tube with an inner diameter of 0.5 mm, able to move in direction transversal to the collector. The negative pole is connected to the collector, consisting of a rotating cylinder of 20 cm×8 cm (l×d); nanofibroin parts are obtained in this way in the form of hollow cylindrical bodies, which are then cut lengthwise and laid out to form generally flat parts. Several samples of electrospun fibroin parts are produced using the following experimental parameters: concentration of fibroin=8% by weight; voltage=24 kV; flow=3 mL/h; spinneret/collector distance=10 cm; harvest time=6 hours. At the end of electrospinning, the fibroin parts are detached from the collector, treated with a water-alcohol solution for 30 min at room temperature and air-dried. These parts have an average thickness of 50 μm.

Example 3

The test described in this Example is intended to determine the amount of ionic liquid which may be retained in different parts of nano- or microfibrous fibroin.

The properties of the four microfibrous fibroin fabrics mentioned in Example 1 (organdie, crêpe, twill and nonwoven fabric) and of a part of nanofibrous fibroin of Example 2 are evaluated.

The ionic liquid used for the test is 1-ethyl-3-methylimidazolium acetate.

The test is carried out according to two impregnation methods, by immersion of the samples in the liquid followed by draining dripping by gravity, and by surface deposition with a brush. In both cases, the amount of liquid retained immediately after the impregnation and after squeezing is evaluated, measured as a percentage by weight with respect to the sample weight; squeezing is carried out by compressing the samples obtained by immersion with a force of 0.5 kg/cm$^2$ for 60 minutes, and compressing the samples obtained by surface deposition with a force of 0.1 kg/cm$^2$ for 2 minutes. The obtained results are shown in Table 1.

TABLE 1

| | Amount of liquid retained by the sample (% by weight) | | | |
|---|---|---|---|---|
| | Immersion | | Surface deposition | |
| | Without squeezing | After squeezing | Without squeezing | After squeezing |
| Nanofiber | 503 ± 124 | 55 ± 12 | 81 ± 8 | 11 ± 1 |
| Organdie | 394 ± 16 | 18 ± 2 | 131 ± 4 | 16 ± 4 |
| Crêpe | 280 ± 8 | 6 ± 3 | 154 ± 15 | 40 ± 4 |
| Twill | 325 ± 6 | 6 ± 2 | 155 ± 23 | 35 ± 10 |
| TNT | 4850 ± 750 | 22 ± 2 | n/a | n/a |

Example 4

Coupling of nano- and microfibrous parts according to the invention.

A sample of organdie fabric and one of crêpe fabric of Example 1, and a sample of nanofibrous part of Example 2, having a size of 3×5 cm, are treated with ionic liquid with surface coating and squeezing as in Example 3.

An organdie/nanofibrous part hybrid structure and a crêpe/nanofibrous part hybrid structure are then produced with the materials thus impregnated, introducing the coupled materials in the apparatus schematized in FIG. 1.

Each pair of materials is introduced in said apparatus with the microfiber layer (organdie or crêpe) at the bottom, in direct contact with the heating plate; a slight pressure (0.1 kg/cm$^2$) is applied to the top plate. The apparatus is placed in a thermostatic chamber to prevent heat losses, and the temperature of the bottom plate is raised to 55° C. for 5 minutes. At the end of this period, the apparatus is removed from the thermostatic chamber and allowed to cool down to room temperature (in about 10 minutes), after which a mixture at a concentration of 80% w/w of ethyl alcohol in water is injected between the two plates with a syringe.

The plates are then opened and the hybrid structure is transferred in a bath of the same water-alcohol mixture to remove all traces of residual ionic liquid; the hybrid structure is left in this bath for 24 hours.

At the end of this period, the hybrid structure is rinsed in distilled water to remove the alcohol and placed between several layers of paper towels which are changed periodically until complete drying of the structure (taking about 12 hours).

Example 5

Chemical characterization of nano- and microfibrous hybrid structures of the invention.

The amino acid composition of separate fibroin microfibrous and nanofibrous parts and of the hybrid structure obtained in Example 4 was evaluated.

About 25 mg of material for each of the three samples were hydrolyzed with HCl 6 N, at 105° C., for 24 hours under vacuum. The hydrolysate solutions thus obtained were analyzed with an automatic ion exchange amino acid analyzer. The results of the analysis are shown in Table 2.

TABLE 2

| | Amino acids (mol %) | | |
|---|---|---|---|
| | Micro part | Nano part | Hybrid structure |
| Aspartic acid | 1.91 | 1.66 | 1.55 |
| Threonine | 1.22 | 0.84 | 1.49 |
| Serine | 11.10 | 10.57 | 11.10 |
| Glutamic acid | 1.25 | 1.48 | 1.34 |
| Proline | 0.68 | 0.84 | 0.82 |
| Glycine | 43.82 | 44.88 | 44.47 |
| Alanine | 29.34 | 29.54 | 28.93 |
| Cystine | — | — | — |
| Valine | 2.28 | 2.31 | 2.10 |
| Methionine | — | — | — |
| Isoleucine | 1.08 | 0.94 | 1.32 |
| Leucine | 0.65 | 0.45 | 0.68 |
| Tyrosine | 4.80 | 4.73 | 4.54 |
| Phenylalanine | 0.37 | 0.56 | 0.46 |
| Lysine | 0.53 | 0.31 | 0.44 |
| Histidine | 0.30 | 0.23 | 0.25 |
| Arginine | 0.66 | 0.67 | 0.50 |
| Total | 100.00 | 100.00 | 100.00 |

Example 6 (Comparative)

Coupling of nano- and microfibrous parts according to prior art.

For comparison purposes, four samples consisting of coupled fibroin nanofibers and microfibers are produced following the procedure of document CN 101879330 A.

Using the same starting materials of Example 4, two hybrid structures are produced in accordance with the following procedure:
- the nanofiber part and the microfiber fabric (organdie or crêpe) are brought into contact and impregnated with an aqueous solution of fibroin at 4% by weight;
- the resulting coupled system is treated at 60° C. for 30 minutes and subsequently immersed in a water-alcohol solution at 80% w/w of methanol for 15 minutes;
- the two coupled systems are then subjected to drying at room temperature, under controlled conditions of temperature and humidity (20° C., 65% relative humidity).

The two samples of hybrid structure thus obtained are hereinafter referred to as "SF Film".

Example 7 (Comparative)

Coupling of nano- and microfibrous parts according to the prior art.

The procedure of Example 6 is repeated, the only difference being that after bringing the fibroin parts into contact and impregnating them with the aqueous fibroin solution at 4% by weight, the system is consolidated by freezing at −20° C. and subsequent freeze-drying.

The two samples of hybrid structure thus obtained are hereinafter referred to as "SF Gel".

Example 8

Morphological characterizations of nano- and microfibrous hybrid structures of the invention and of the prior art.

The organdie/nanofibrous part hybrid structure produced in Example 4 was observed with scanning electron microscope (SEM, mod. MIRA 3, Tescan). For comparison, samples of organdie fabric and of nanofibrous part were also observed before coupling. The organdie fabric was chosen as the open arrangement of the warp and weft yarns leaves some gaps through which it is possible to characterize the surface of the nanofibrous part on the side adjacent to the microfibrous part (coupling side).

For this purpose, 0.5×0.5 mm samples were taken from the hybrid structure, positioned on aluminum sample-holders for SEM with a double-sided adhesive tape, and coated with gold-palladium by sputtering. Both sides exposed to the air were examined, that of the microfibers and that of the nanofibers.

Figure 2:
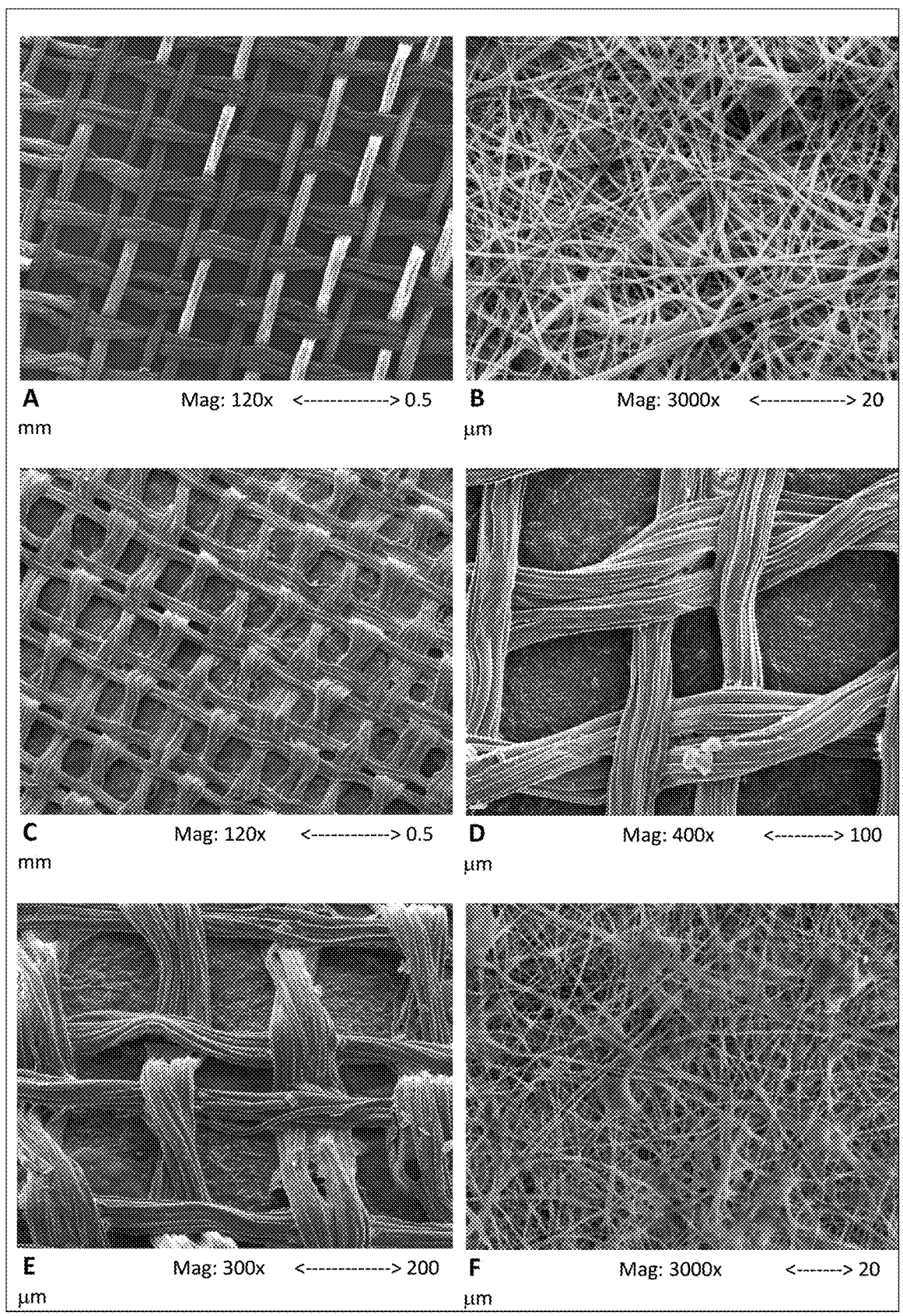
FIGS. 2 and 3 show photomicrographs obtained with scanning electron microscope (SEM) of samples of hybrid structures produced according to the invention.

Photomicrographs of the samples are shown in FIG. 2.

FIG. 2-A and FIG. 2-B show the microfibrous organdie fabric and the nanofibrous part, respectively, before coupling; the latter has the typical features of a substrate obtained by electrospinning, with fibroin nanofibers having an average diameter of 500-600 nm, laid irregularly (as non-woven fabric) and with a very fine porosity. After coupling, the microfibrous part (FIG. 2-C) displays a slight flattening of the component yarns, probably due to the pressure exerted in the various steps of the coupling process; the warp and weft yarns however still retain their original structure and the individual microfibers of which they are made are still well visible.

Among the pores of the fabric (FIGS. 2-D and 2-E), the surface of the coupled nanofibrous part may be seen, which retains the typical roughness visible at low magnification; in some areas (FIG. 2-E), partly gelified areas may be seen with more evidence which connect microfibers and nanofibers and keep them in close contact.

FIG. 2-F shows the surface of the nanofibrous part exposed to air after coupling. Although there are fusion areas of the nanofibers, the typical morphology observed for the untreated native part is retained.

Figure 3:
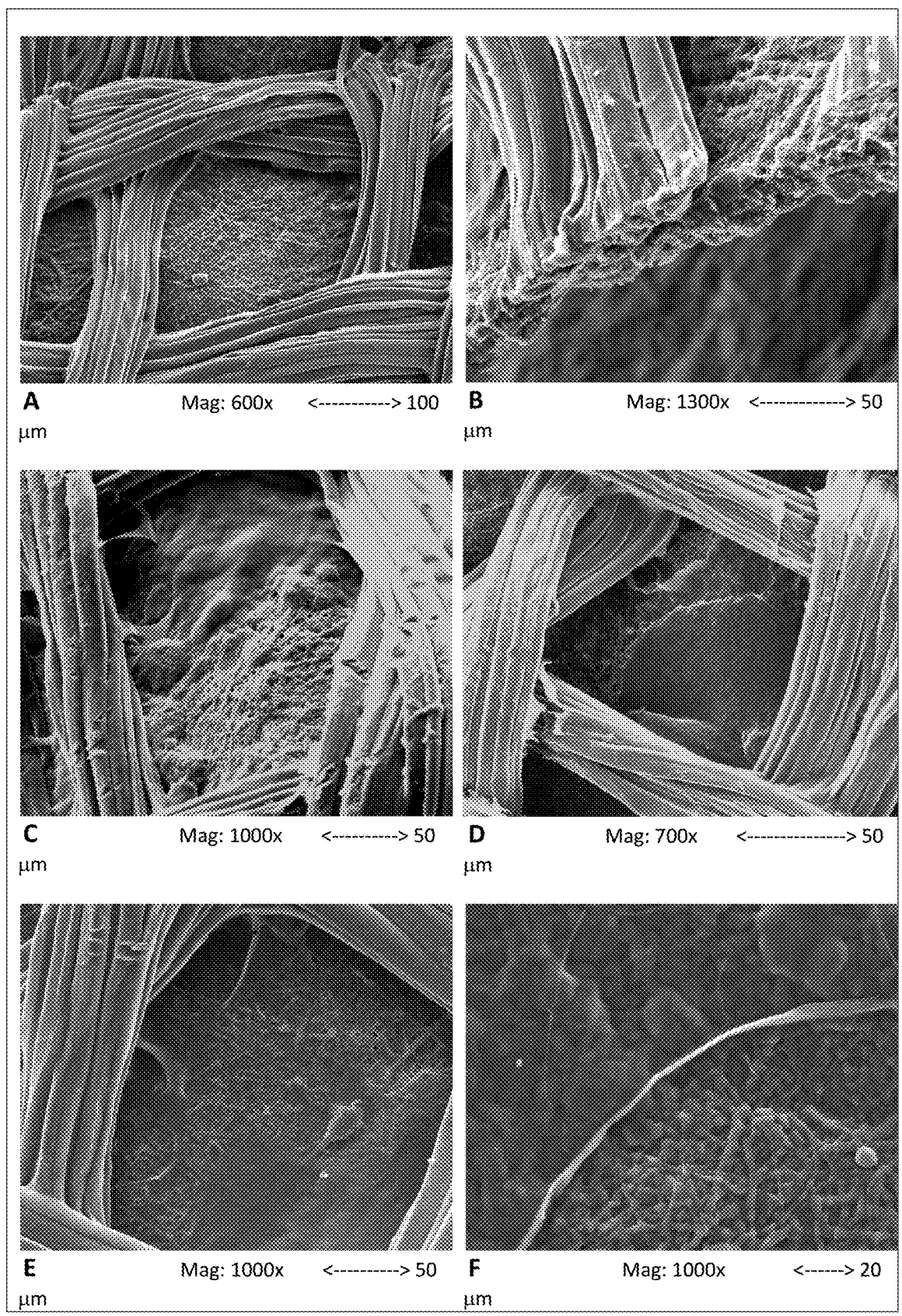

FIGS. 3-A and 3-F (especially FIG. 3-F) show the presence of a thin layer of gel which coats both the microfibers and the nanofibers, connecting them with interfibrous connections. The gel layer is extremely thin and superficial, showing through the surface of the single microfibers and also that of the nanofibers, whose morphology is only slightly deformed on the surface while it is substantially retained in the remaining part of the material.

Finally, FIG. 3-B shows a peripheral area of the hybrid structure, along the edge of the cutting with which the sample subjected to SEM observation was taken. This image shows that the coupling process of the invention is effective and that the two coupled parts do not separate even if subjected to deformation and compression, as usually happens in the area subject to cutting with scissors or scalpel.

Figure 4:
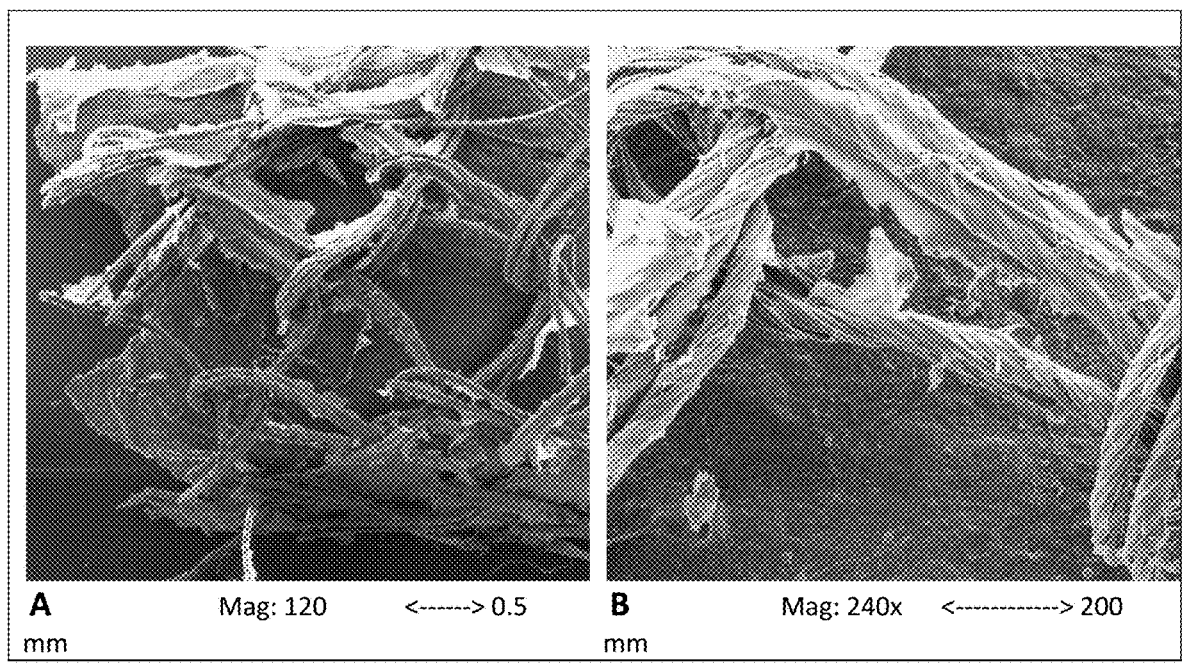
FIG. 4 shows photomicrographs similar to those in FIGS. 2 and 3 obtained on samples of hybrid structures produced according to the prior art.

For comparison, a sample of the prior art is examined under SEM, produced according to the procedure of comparative Example 6 (organdie "SF Film" sample). The images of this sample are shown in FIGS. 4-A and 4-B, and they show the presence of a film on the surface of the microfibers, crushed and adhering only to the latter and unable to serve as an effective adhesive with the nanofibrous part.

Example 9

Chemical-Physical Characterization of Hybrid Structures of the Invention.

The organdie/nanofibrous hybrid structure produced in Example 4 is further characterized by Fourier transform infrared (FTIR) spectroscopy in order to verify whether the coupling process causes changes in the physical-chemical, structural and conformational properties of the micro- and nanofibrous components.

A NEXUS Thermo Nicolet spectrometer in ATR (Attenuated Total Reflectance) mode was used, with Smart Performer accessory equipped with a SeZn crystal cell. FTIR spectra were recorded in the wavenumber range 4000-700 $cm^{-1}$, accumulating 64 scans at a resolution of 4 $cm^{-1}$. Each spectrum is the average of three measurements (FIG. 5).

The spectral region 1900-700 $cm^{-1}$ represents the fibroin fingerprint from the point of view of the composition and structure of the polymer. The most significant conformationally sensitive bands are known as Amide I (1615-1690 $cm^{-1}$), Amide II (1509 $cm^{-1}$), and Amide III (1230-1260 $cm^{-1}$), derived from a multiplicity of vibrational modes of the peptide bond. Amide I is mainly due to stretching vibrations of the CO bond, with a contribution of the CN bond; Amide II is due to the bending of the NH bond (predominant) with the contribution of the stretching of the CN bond; Amide III is due to NH bending and CN stretching vibrations.

Figure 5:
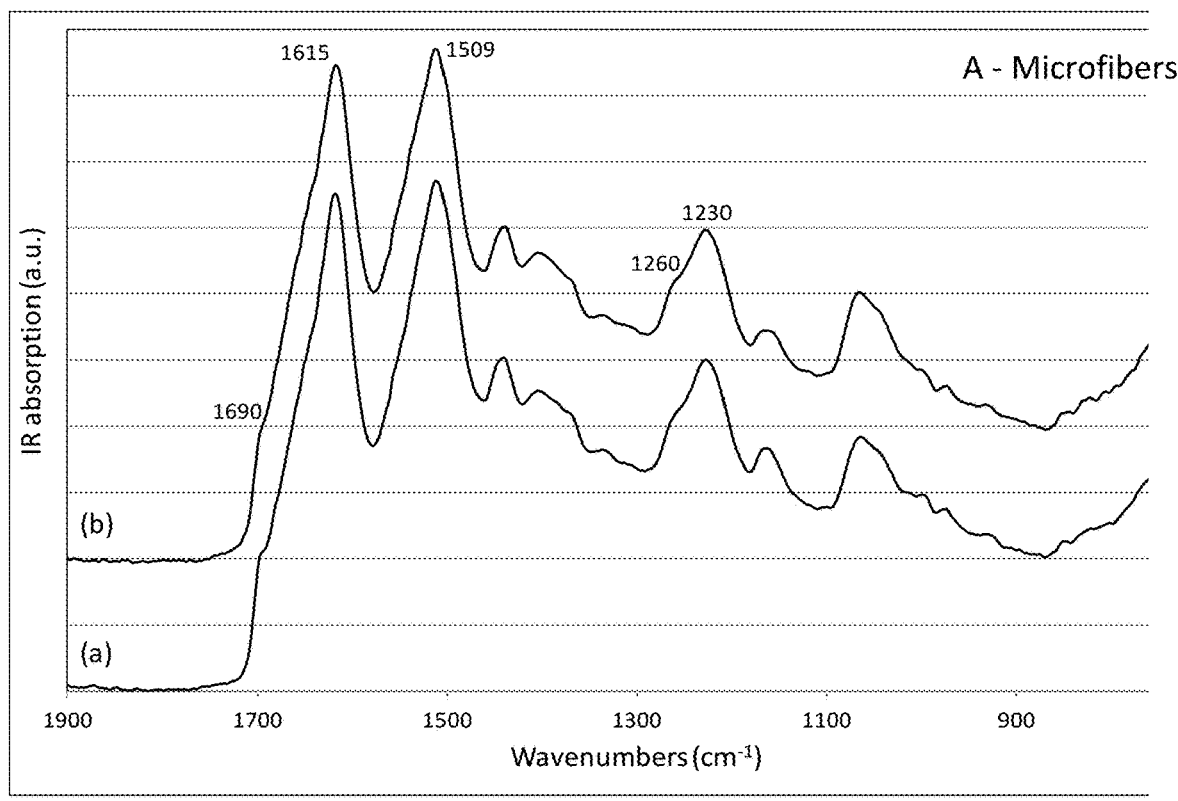
FIG. 5 shows the IR spectra of hybrid structures produced according to the invention compared with samples of fibroin microfibers alone or fibroin nanofibers alone.
Figure 5:
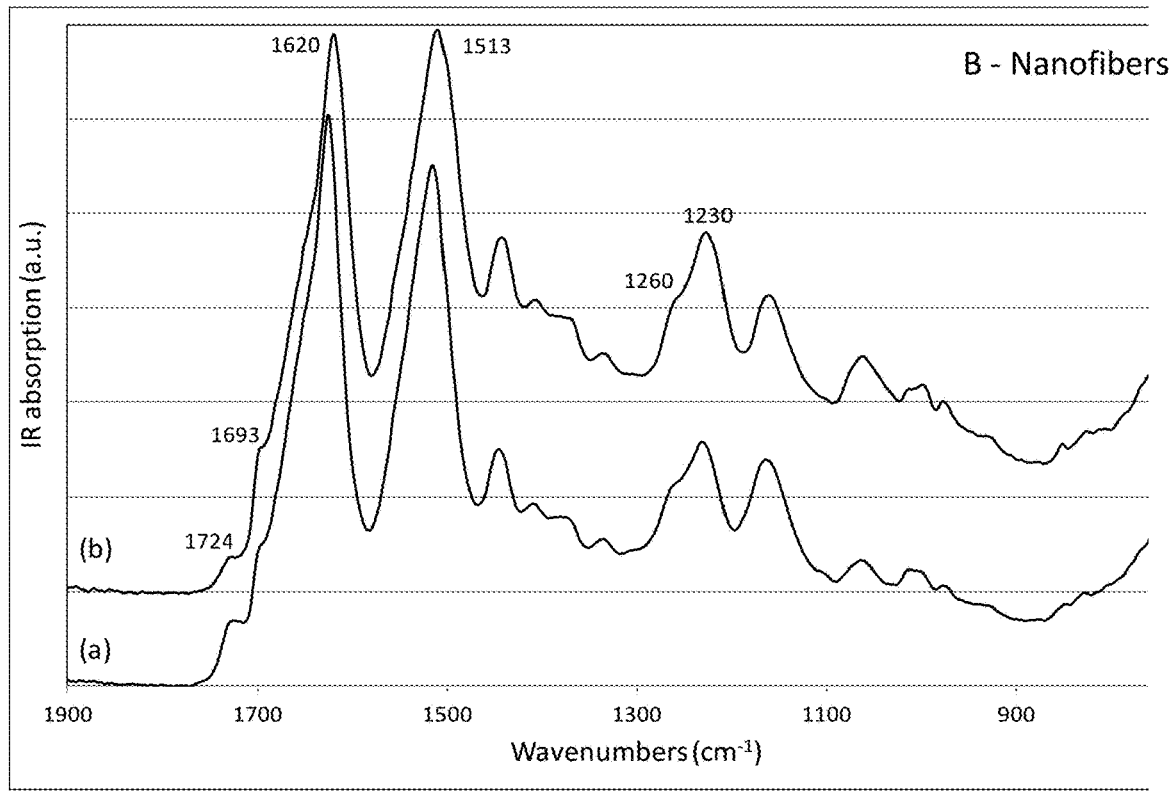

FIG. 5-A shows, overlapped, the spectrum of microfibers before treatment (curve (a)) and of the hybrid structure of invention (curve (b)); similarly, FIG. 5-B shows, overlapped, the spectrum of nanofibers before treatment (curve (a)) and of the hybrid structure of invention (curve (b)).

Based on the position and intensity of the bands of Amide I, II and III in the spectra, it can be deduced that both the microfibers and the nanofibers, before the coupling treatment, have the typical β-sheet molecular conformation, characteristic of native (microfibers) or regenerated (films, nanofibers, etc.) crystalline fibroin materials.

The spectral profiles after coupling are exactly superimposed to those of the respective untreated samples, indicating that the structural features of the material are retained.

The two components of the band of Amide III were used to calculate the crystallinity index of the materials before and after the coupling process. The crystallinity index is obtained from the ratio between the intensity of the band at 1260 $cm^{-1}$ and that of the band at 1230 $cm^{-1}$ ($C_1 = I_{1260}/I_{1230}$). For microfibers, this index remains essentially unchanged after coupling, changing from 0.52 to 0.51, while for nanofibers it decreases by about 8%, from 0.60 to 0.55. This behavior is consistent with the transformation of a fraction of the nanofibrous part that during the gelification process and the subsequent coagulation takes a less orderly structure than the pre-existing one, changing into a transition phase with adhesive properties, as shown by the photomicrographs in Example 8.

Example 10

Structural Characterization of Hybrid Structures of the Invention.

The organdie/nanofibrous part hybrid structure produced in Example 4 is further characterized by differential scanning calorimetry (DSC).

Figure 6:
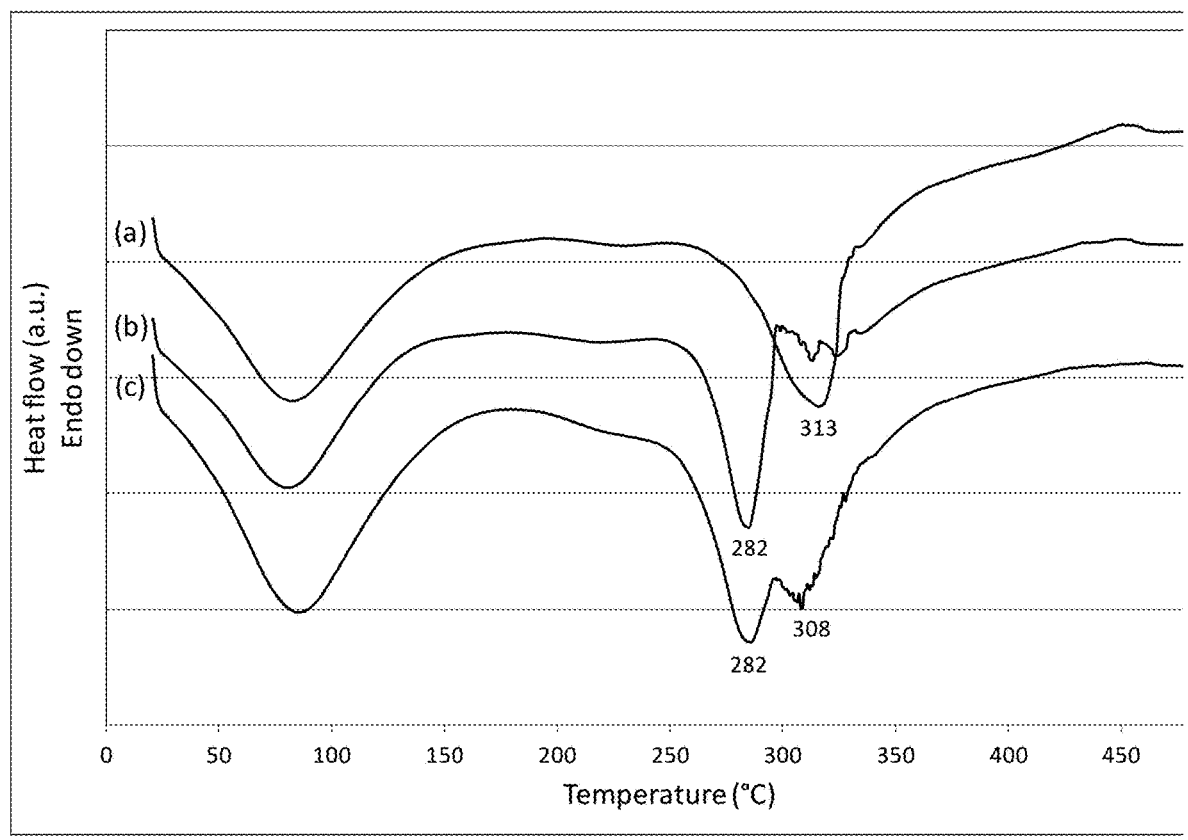
FIG. 6 shows graphs of differential scanning calorimetry (DSC) relating to hybrid structures produced according to the invention and to fibroin microfibers alone or fibroin nanofibers alone.

A calorimeter 200 Q TA Instruments is used, recording the curves from room temperature to 500° C. with heating rate of 10° C./min under nitrogen flow; each sample, weighing about 5 mg, was introduced in aluminum crucible and analyzed in duplicate. The test results are shown in FIG. 6, which shows the thermograms for microfibers alone (curve (a)), for nanofibers alone (curve (b)) and for the hybrid structure of the invention (curve (c)).

As can be seen, all curves show a first endotherm at a T below 100° C. which can be ascribed to the evaporation of the moisture contained within the material.

In the case of microfibers, a second, very intense endotherm follows, with peak at 313° C., attributed to the thermal degradation of fibroin in the form of crystalline and oriented fiber with β-sheet conformation.

The thermogram of nanofibers before treatment (curve (b)) has a similar profile, in which however the second endotherm is at lower temperature (282° C.), indicating a much lower orientation degree of the crystalline phase and much more irregular crystal size than in the case of microfibers.

The thermal diagram of the hybrid structure sample (curve (c)) shows the characteristic transitions of the two component parts: the degradation peak of nanofibers at 282° C. remains unchanged, while that of microfibers moves to 308° C., possibly due to intermolecular interactions in the areas of very close mutual contact present in the coupled materials of the invention.

Example 11

Mechanical Characterization of Hybrid Structures of the Invention and of the Prior Art.

Tensile tests are carried out on a sample of Example 4, consisting of the coupling of a nanofibrous part (50 μm thickness) and of an organdie weave fabric as microfibrous component (90 μm thickness); for comparison, also the properties of strips of the separate nanofibrous part and of the microfibrous fabric were measured.

The thickness of the samples before and after coupling was measured according to the standard UNI EN ISO 5084:1998 method. The obtained values were used to calculate the mechanical parameters of stress and modulus. The mechanical properties were measured on strips of parts as such and of hybrid structure, having a size of 20×10 mm (length×width), using an Instron dynamometer mod. 4501, at 10 mm gauge length, and 10 mm/min crossbar rate. The measurements were carried out in standard atmosphere at 20° C. and 65% relative humidity. The stress, deformation and modulus values were calculated from the load-elongation curves and they represent the average of ten measures for each sample.

Figure 7:
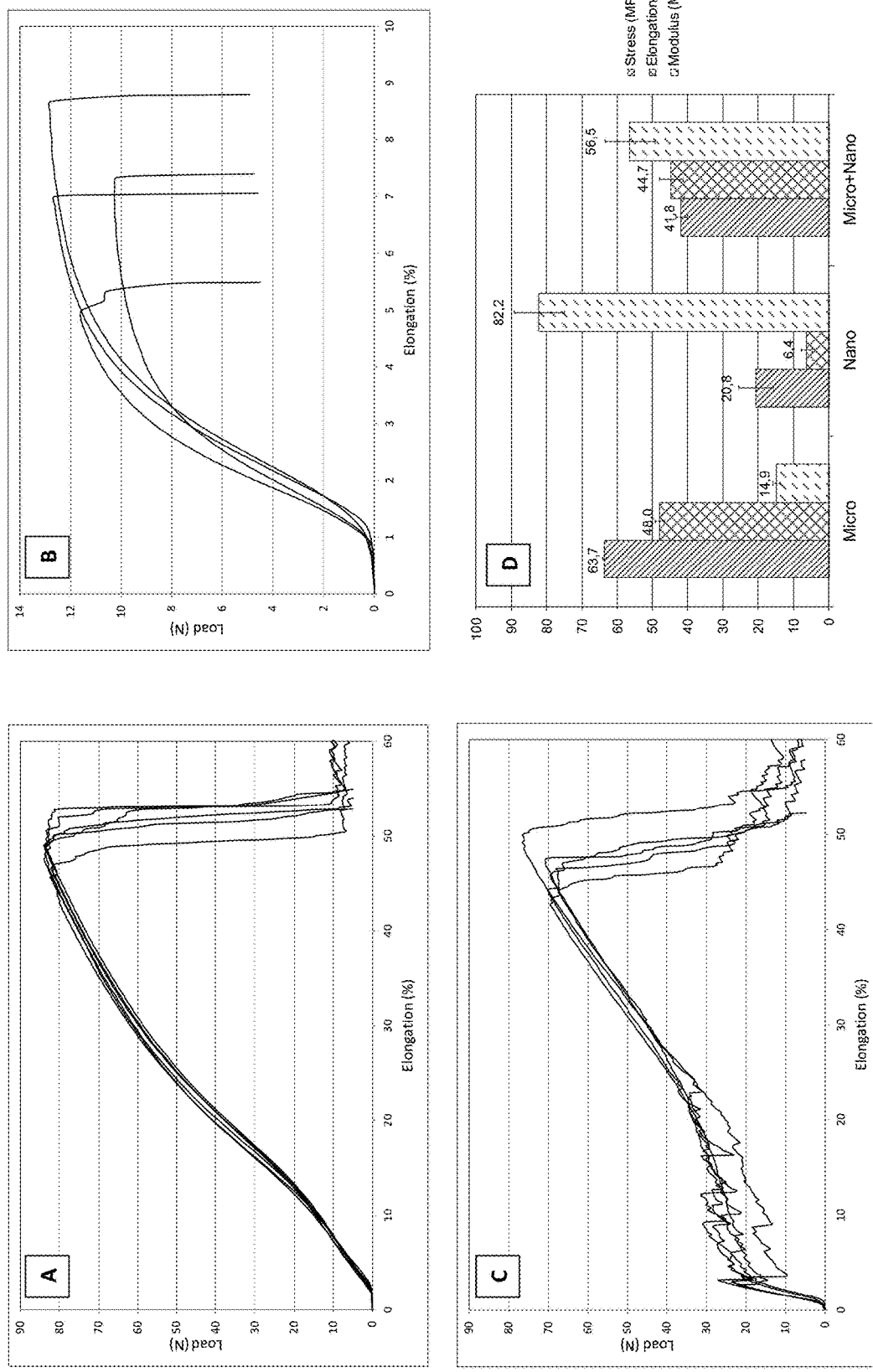
FIG. 7 shows load/elongation diagrams of samples of hybrid structures produced according to the invention and of fibroin microfibers alone or fibroin nanofibers alone.

The obtained results are shown in the graphs in FIG. 7 and summarized in Table 3.

The load-elongation curves of the microfibrous part (FIG. 7-A) are characterized by an initial step of stretching of the yarns that make up the textile structure. Once stretched, an additional elongation occurs ascribable to the inherent characteristics of elasticity of the yarn, which oppose an increasing resistance to elongation itself, as shown by the gradual increase of the load values. Finally, breaking occurs after an elongation of about 50%. The salient features of this part are a high toughness, an equally high elongation and a relatively low initial modulus.

Conversely, the nanofibrous part (FIG. 7-B), has a diametrically opposite mechanical tensile response: low toughness and elongation values, very high initial modulus.

The hybrid structure of the invention (FIG. 7-C) displays a mechanical behavior that is not simply the result of the sum of the individual components of the system, but rather, it displays deviations from additivity which account for a very strict and specific interaction between the two component parts. In fact, the hybrid structure is characterized by a very high initial resistance to the applied load. This resistance is attributed to the close interaction between the two parts at their interface. As the load increases, the load-elongation curves become jagged, which is attributed to the sequential rupture of the contact points between the microfibrous and nanofibrous parts. This phase extends to elongation values of 20-25%, significantly higher than those of the nanofibrous part as such, which does not stretch more than 6-7%. The further increase in load brings out the contribution of the microfibrous part which then breaks for elongations between 45% and 50%, a value very similar to that of the part as such.

The mechanical values measured during the tests, also including stress and modulus, are shown in FIG. 7-D and summarized in Table 3.

TABLE 3

|  | Microfibers | Nanofibers | Hybrid Micro/Nanofibers |
| --- | --- | --- | --- |
| Stress (MPa) | 63.7 ± 0.5 | 20.8 ± 5.0 | 41.9 ± 1.6 |
| Elongation (%) | 48.0 ± 1.3 | 6.4 ± 1.5 | 44.7 ± 3.3 |
| Modulus (MPa) | 14.9 ± 1.1 | 82.2 ± 7.0 | 56.5 ± 7.2 |

Example 12 (Comparative)

For comparison, the test of Example 11 is repeated on a sample of the prior art ("SF Gel" sample with organdie fabric, produced as described in Example 7).

A sheet of porous fibroin alone was also produced, following the same procedure and pouring the aqueous solution, before freezing and freeze-drying, into a mold. 20×10 mm strips of these samples were subjected to the same test as the previous Example, in identical conditions.

Figure 8:
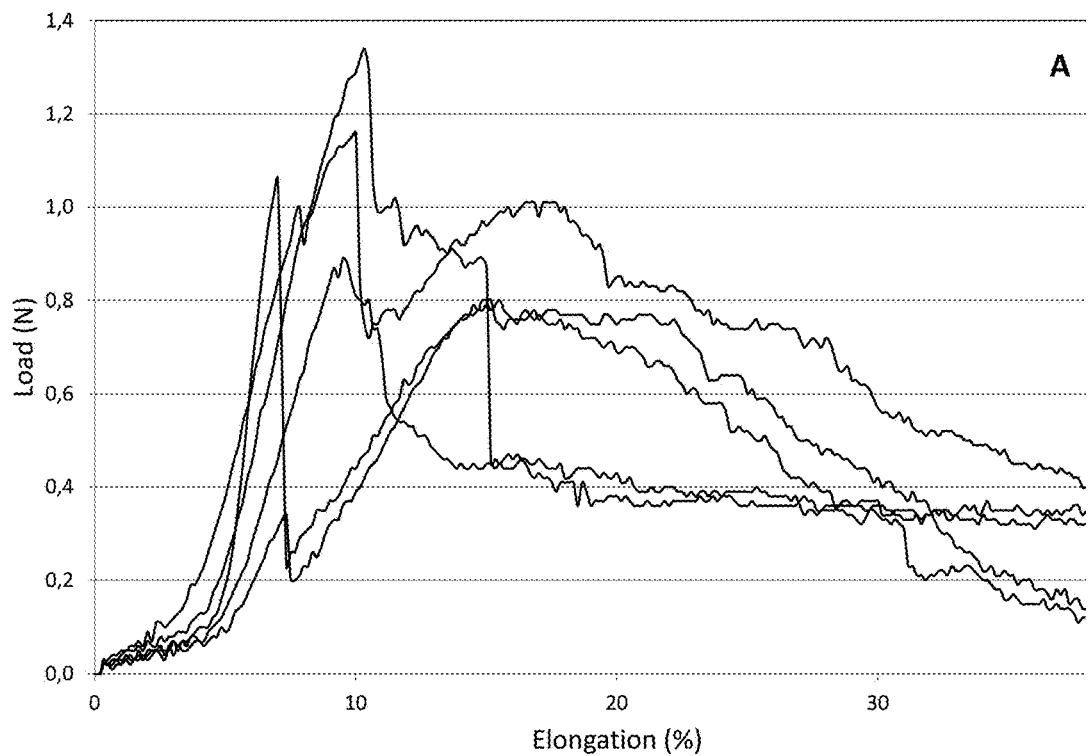
FIG. 8 shows load/elongation diagrams of samples of hybrid structures produced according to the prior art.
Figure 8:
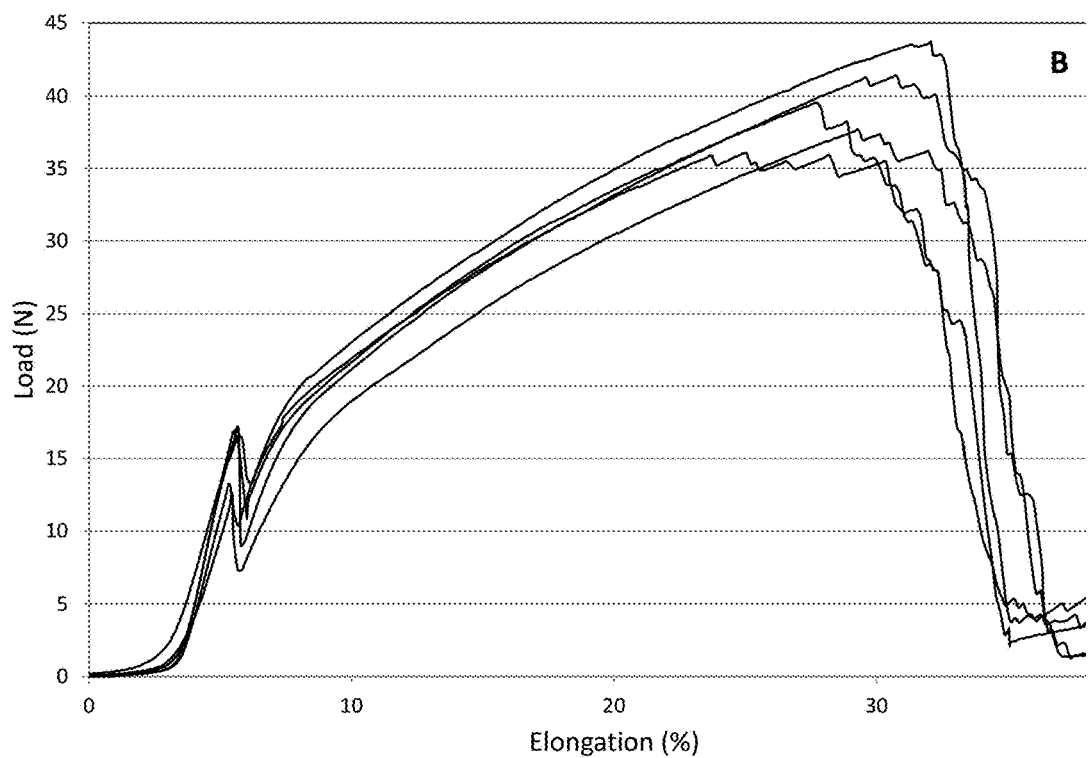

The results are shown in FIG. 8 for the porous sheet (A) and for the micro/nano hybrid structure (B), respectively.

The porous sheet (FIG. 8-A) has very poor mechanical properties: the average value of load strength is 1.1±0.2 N, about 10 times lower than a nanofibrous part (11.2±1.8 N: see FIG. 7-B); the variability of the curve shape is due to the heterogeneity of the texture of porous materials of silk fibroin obtained with the method described above.

The load-elongation curves of the micro/nano hybrid structure (B) coupled using porous fibroin (FIG. 8-B) are characterized by the presence of two peaks, one at low and the other at high deformation values. The peak at low deformation corresponds to the breaking of the nanofibrous component, as indicated by the load and elongation at break values (15±2 N and 5.5±0.2%, respectively).

The peak at high deformation corresponds to the breaking of the microfibrous substrate (load: 40±3 N; elongation at break: 29±3%).

Example 13

Measurement of the Adhesion Strength of Hybrid Structures of the Invention and of the Prior Art.

Two samples of the invention of Example 4, prepared from organdie and crêpe fabrics, and two samples (organdie and crêpe) for each of the "SF Film" and "SF Gel" materials of the prior art, produced as described in Examples 6 and 7, respectively, are subjected to mechanical tests designed to measure the adhesion strength between the two micro and nanofibrous components of the hybrid structures. The tests were carried out using an Instron dynamometer mod. 4501, according to the standard UNI EN ISO 13937-2:2000 method.

Figure 9:
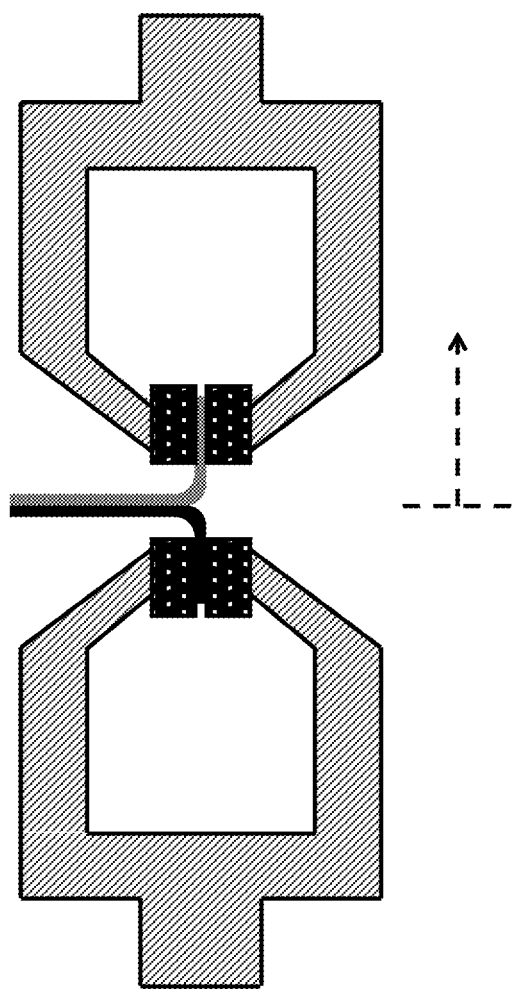
FIG. 9 schematically shows an apparatus for carrying out peeling tests on the layers of hybrid structures.
Figure 10:
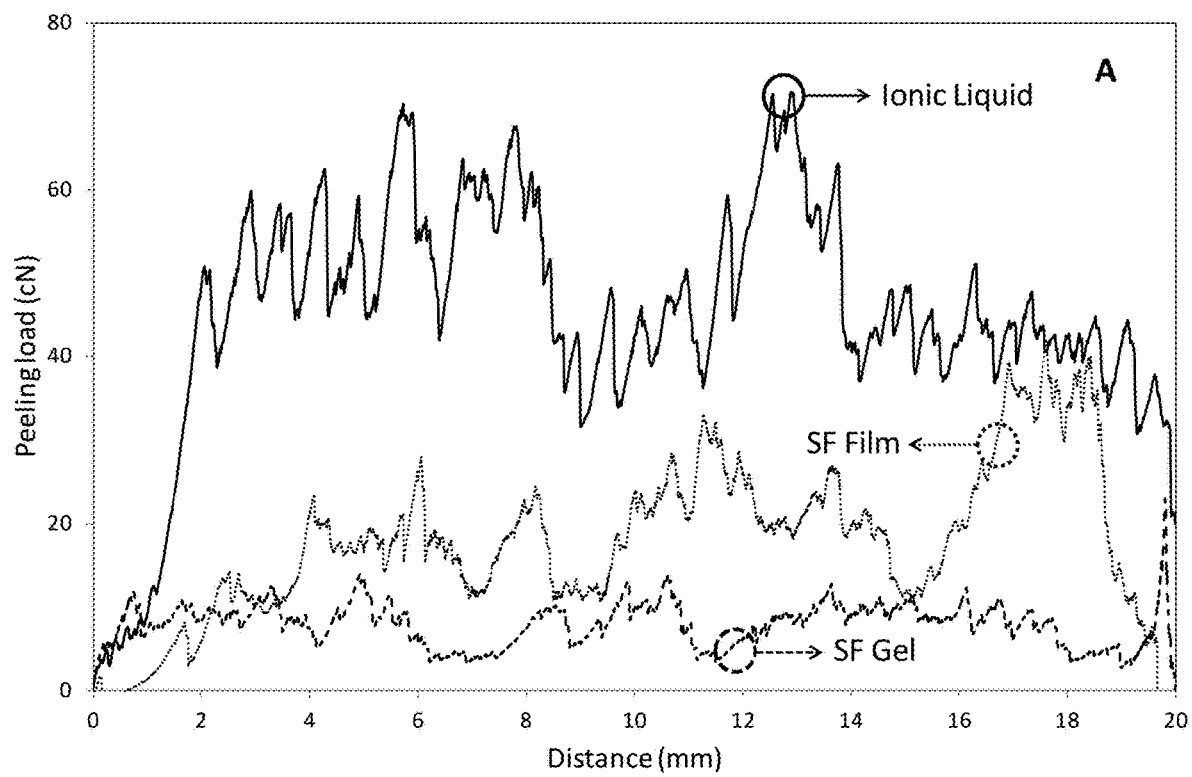
FIG. 10 shows the graphs of applied force/peeling stroke obtained in tests of detachment of the layers of hybrid structures of the invention and of the prior art.
Figure 10:
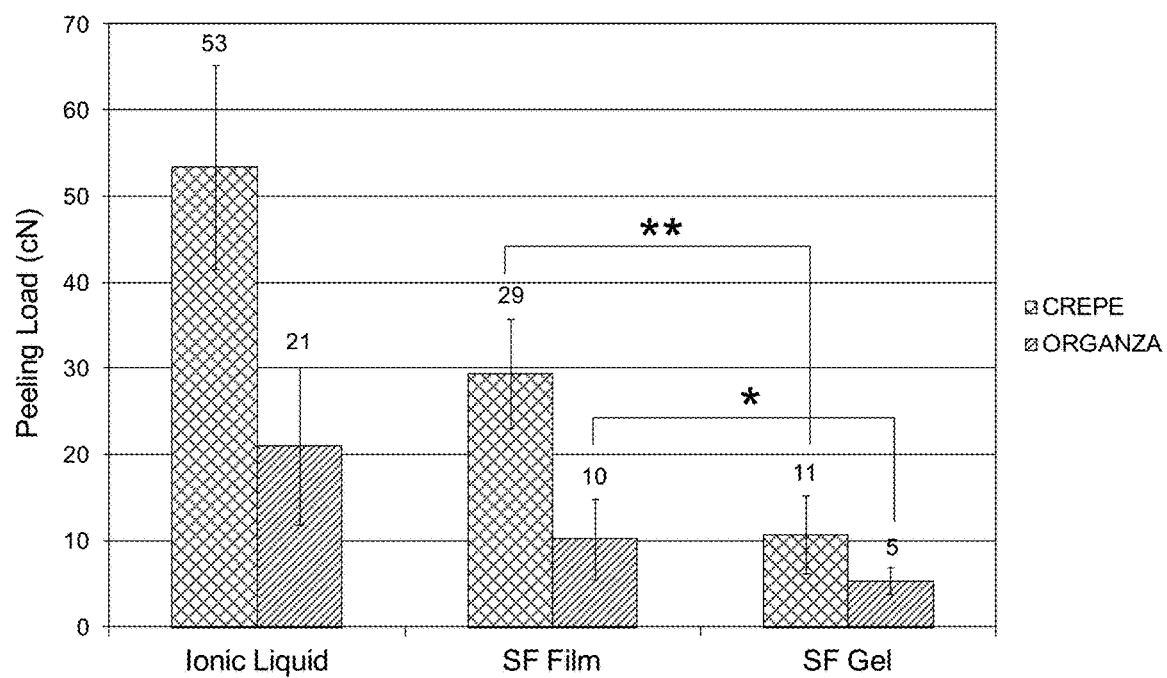

In particular, 10×40 mm rectangular strips are taken from each of the samples. At one end of the sample, the two flaps, one corresponding to the nanofibrous part and one to the microfibrous part, were delicately separated by a stretch of about 10 mm; these flaps were locked into the grips of the dynamometer, as shown in FIG. 9. The top (movable) grip was then actuated, moving it away from the bottom (fixed) one at 2 mm/min crossbar rate, and the force required (measured in cN) to cause the separation of the microfibrous (lower) part from the nanofibrous (upper) part was recorded continuously for a stretch of at least 20-30 mm. At least 5 tests were carried out for each sample and the single results were averaged. Typical "peel load/stroke" curves are shown in FIG. 10-A. The results obtained from the processing of experimental data are shown in Table 4 and in the bar chart in FIG. 10-B.

TABLE 4

| | Separation force (cN) | | | | | |
|---|---|---|---|---|---|---|
| | Invention | | "SF Film" | | "SF Gel" | |
| | Mean | Maximum | Mean | Maximum | Mean | Maximum |
| Crêpe Microfiber | 53 ± 11 | 72 ± 12 | 29 ± 6 | 58 ± 9 | 11 ± 5 | 18 ± 5 |
| Organdie Microfibers | 21 ± 9 | 31 ± 11 | 10 ± 5 | 24 ± 10 | 5 ± 2 | 9 ± 2 |

Example 14

In Vitro Cytotoxicity and Genotoxicity Studies.

In view of the application for the production of scaffolds for implantation in the human and animal body, the in vitro biological properties of the composite materials of the invention were evaluated.

The tests were conducted with two human cell models, human fibroblasts (MGM18004E) and human endothelial cells (HUVEC).

Human fibroblasts were cultured in DMEM culture medium with a high glucose content (Gibco) containing 20% bovine fetal serum inactivated by heat treatment (Gibco), 200 mM L-glutamine (Euroclone), penicillin and streptomycin (Euroclone).

Human endothelial cells were cultured in EBM-2 (basal medium for endothelial cells 2, Lonza) culture medium, containing penicillin and streptomycin (Euroclone).

Analytical tests were designed to assess the degree of cell proliferation and DNA damage as markers of potential cytotoxicity and genotoxicity of the biomaterial.

The Alamar Blue® test measures the metabolic activity of cells, which is directly linked to cell proliferation. The cells were seeded in 96-well plates at an initial density of 6000 cells/cm$^2$. Culture medium alone and cells alone were used as blanks. The tests were carried out in technical triplicate and biological duplicate. Cells were cultured for 24, 72 and 120 hours in an incubator at 37° C., in the presence of 5% $CO_2$. The culture medium was changed on day 3. At the end of the incubation period, a fixed volume of Alamar Blue® (10% of total volume) was added to the well. After a further incubation period of 18 hours, the medium was transferred to another plate and the absorbance values at 570 nm and 600 nm were recorded with a multidisc reader (Biotech). Results were expressed as percentage difference between samples with cells alone and samples into contact with the biomaterial of the invention.

The DNA damage test evaluates the possible genotoxicity of the biomaterial by detecting the presence of phosphorylated $Ser_{139}$ in the H2AX histone. Phosphorylation is induced by the presence of ruptures in the DNA double strand by immunofluorescence. The cells were seeded at an initial density of 6000 cells/cm$^2$ for 24 hours, 3000 cells/cm$^2$ for 120 hours, and 1500 cells/cm$^2$ for 120 hours. The culture medium was changed on day 3. Cells treated with 200 mm $H_2O_2$ for 16 hours were used as positive control. At the end of the experiment, cells were fixed with 4% paraformaldehyde (Sigma-Aldrich), followed by permeabilization with phosphate saline buffer solution (PBS) containing 0.1% BSA (Bovine Serum Albumin) and 0.25% Triton X-100. Non-specific reaction sites were blocked by incubation with blocking buffer (0.1% BSA in PBS). Subsequently, an anti-γH2AX antibody was incubated for 1 hour, and revealed through a secondary goat antibody Alexa Fluor® 555 anti-mouse IgG. The cell nuclei were marked with Hoechst 33342. The plates were examined with a Leica DMI4000B fluorescence microscope (Leica Microsystems) at 20×. The average number of positive cells to DNA damage was determined by observing 3-5 independent fields for each biological repetition and for each experimental condition.

Figure 11:
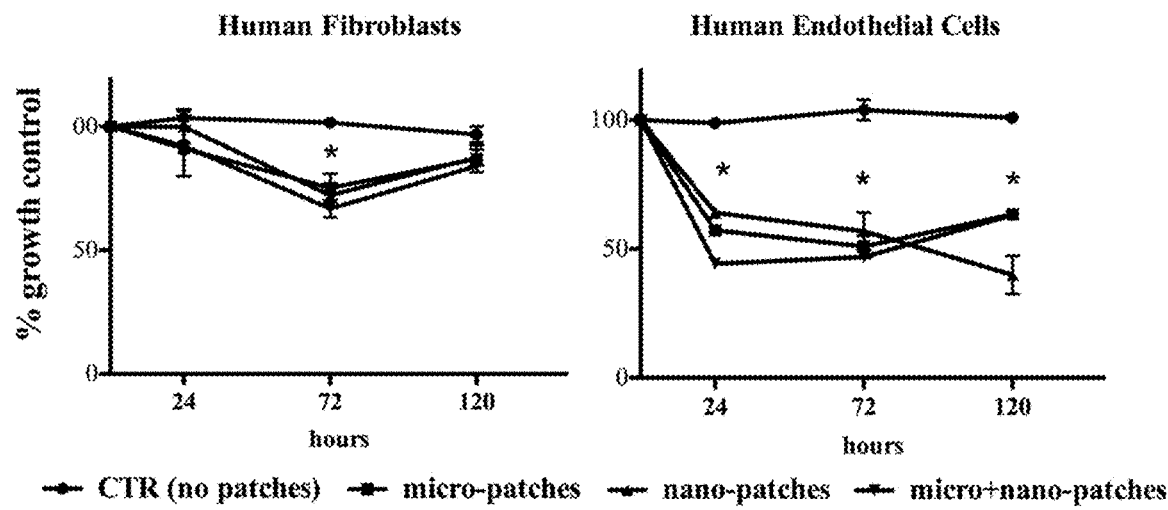
FIG. 11 show graphs representative of cell growth on medical devices made with hybrid structures of the invention.

FIG. 11 shows the cellular growth curves, expressed as a percentage of the control growth. At 24 hours, human fibroblasts show a degree of proliferation similar to that of cells seeded into the control well (polystyrene substrate). At 72 hours, a slight decline was observed in the growth curves of cells in contact with the three SF patches (microfibers, nanofibers and micro/nano hybrid), which was immediately recovered at 120 hours. It can be concluded that the rate of human fibroblast proliferation is not disturbed by the presence of three different SF patches.

Human endothelial cells in contact with the three SF biomaterials showed a decline in the degree of proliferation compared to the control. It is worth noting that, as for the test with human fibroblasts, the three SF biomaterials show almost the same trend in terms of cell proliferation up to 72 hours. However, with human endothelial cells at 120 hours with the nanofibrous patch they show a further decline of the curve while the hybrid micro/nanofibrous patches had an increase in the measured metabolic activity of cells, which is directly linked to cell proliferation.

Figure 12:
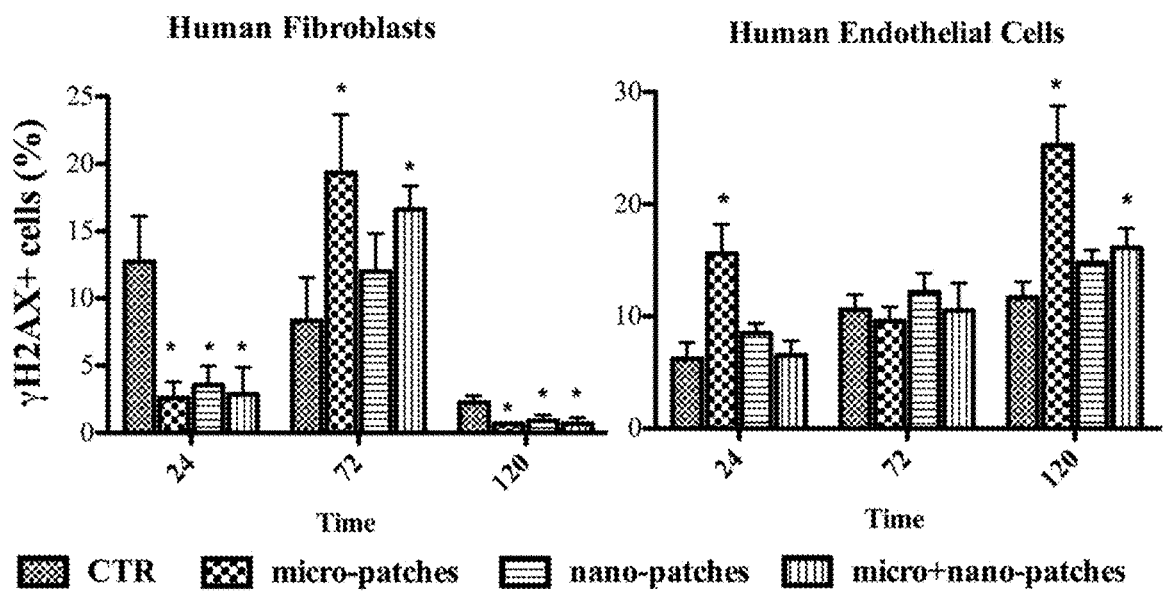
FIG. 12 shows histograms relating to genotoxicity measures on patch samples made with microfibers alone, nanofibers alone and with the hybrid structures made from fibroin of the invention.

The genotoxicity test results (FIG. 12) for human fibroblasts showed an increase in the degree of phosphorylation of H2AX after 72 hours of incubation. This result is in accordance with the trend of the Alamar Blue® proliferation test, which showed a slight decline in the metabolic activity of cells at the same incubation time, probably attributable to an adaptation phase of cells cultured on SF biomaterials. At 24 and 120 hours, the human fibroblasts cultured on three SF biomaterial showed significantly lower levels of phosphorylation compared with control cells cultured on polystyrene, suggesting that the three SF patches are less genotoxic to these cells than the control substrate. As already observed with the Alamar Blue© test, human endothelial cells behave differently from human fibroblasts: only the microfiber substrate induces an increase in the phosphorylated form of H2AX at 24 and 120 hours, indicating a slightly higher genotoxic effect of this SF patch compared to the control substrate. On the other hand, the nanofibrous patch and, most importantly, the micro/nanofibrous hybrid patch displays the DNA damage to a lesser extent, indicating a better biocompatibility in terms of genotoxicity to this type of human cells.

Comment to the Results

As demonstrated by the above tests, the composite materials of the present invention have properties that partly reproduce those of the separate nano- and microfibers, but also new features resulting from the coupling of the two types of fiber (dynamometric tests, FTIR and DSC).

The chemical analysis results show that the hybrid structure has essentially the same amino acid composition of the starting microfibrous and nanofibrous parts, characterized by the presence of large amounts of only 4 amino acids (glycine+alanine+serine+tyrosine=89% moles), while all the other amino acids are present in small amounts (approximately 11% total moles). It can be concluded that the coupling process does not modify the chemical structure of fibroin and that the biological chemotactic properties of the polymer therefore remains unchanged even after coupling.

Moreover, compared to the materials of the prior art, the materials of the invention display better adhesion and a more consistent behavior in mechanical tests.

In particular, the SEM images of hybrid structures of the invention (FIGS. 2 and 3) show good adhesion between the parts and the presence of a continuous polymer film between the fibers of the same two parts, while the similar images of structures of the closest prior art (patent application CN 101879330 A, FIG. 4) show a polymer film, which should guarantee the adhesion between the parts, which is fragmented and adhering to only one of these.

Tensile tests showed that the composite material of the invention has unique features in the elongation area between about 10 and 25%, due specifically to the interactions between the two types of fibers. To the contrary, the coupled material of the prior art shows a behavior that is the pure sum of the behaviors of the nano and microfibrous components (FIG. 8-B), demonstrating that the micro and nano components coupled together by means of porous material behave as separate phases, each retaining its inherent properties, without showing any change/improvement caused by the coupling technique; rather, by producing a hybrid structure according to the closest prior art, a worsening in the tensile properties of the microfibrous component is obtained, changing from load and elongation at break values of about 63 N and 48% to values of 40 N and 30%, respectively.

Similarly, the dynamometric peeling tests of the two layers of the hybrid structures confirmed a much higher adhesion strength between the nano- and microfibrous parts in the case of the present invention than in the case of the prior art (FIG. 10).

The prior art process therefore does not guarantee the same continuity features between the two parts of the final hybrid structure obtained with the process of the present invention: in the case of devices manufactured according to the prior art, this may lead to the production of morphological and mechanical discontinuities among the different layers, resulting in loss of the performance and geometric characteristics, up to yield and/or collapse of the weaker (e.g. nanofibrous) layers from a mechanical point of view. In stressing use conditions from the mechanical and biological point of view, such as those that can occur in the progress of an in vivo implantation, the different behavior of the two or more polymer phases that make up the hybrid structure of the prior art could create local stresses of such a magnitude as to interfere with the regenerative processes in progress, especially if the material is exposed to flows of physiological fluids.

The hybrid structures of the invention showed a better in vitro biological behavior than the individual parts of microfibrous fibroin and of nanofibrous fibroin further enhancing, from the biological behavior point of view, the already good performance levels of micro and nanofibrous parts taken separately: the scaffold performance of microfibroin alone have been described for example in the article "De novo engineering of reticular connective tissue in vivo by silk fibroin nonwoven materials", Dal Pra et al., Biomaterials (2005) 26 1987.

The invention claimed is:

1. An implantable medical device comprising:
   a hybrid structure comprising coupled microfibers and nanofibers of silk fibroin, said hybrid structure obtained according to the process comprising:
   a) preparing of one or more parts made of microfibrous fibroin;
   b) preparing of one or more parts made of nanofibrous fibroin;
   c) treating of said one or more parts of nanofibrous fibroin and of said one or more parts of microfibrous fibroin, separately or after coupling, with a solvent for fibroin and/or with a solution comprising fibroin dissolved in the solvent;
   c') if in step c) the nanofibrous and microfibrous parts have been treated separately with a solvent for fibroin and/or with a solution comprising fibroin dissolved in a solvent, coupling of said parts;
   d) consolidating the hybrid microfibrous/nanofibrous structure obtained in step c) or in step c') by thermal treatment at a temperature between 10° C. and 150° C., for a time between 1 minute and 24 hours;
   e) removing the solvent by washing with water or a water-alcohol mixture at a temperature between 10° C. and 100° C., or by evaporation at a temperature between 10° C. and 100° C.,
   wherein the solvent for fibroin or the solvent of the solution comprising fibroin used in step c) is selected from:
   (i) formic acid, 1,1,1,3,3,3-hexafluoro-2-propanol, trifluoroacetic acid, hexafluoroacetone, N-methylmorpholine N-oxide, ionic liquids, and mixtures thereof, wherein said solvents are pure or in mixture with water;
   (ii) calcium chloride-ethanol-water mixtures, calcium nitrate-methanol-water mixtures, aqueous solutions of lithium salts and;
   (iii) mixtures among the solvents of (i) and (ii).

2. The implantable medical device according to claim 1, wherein the parts of microfibrous fibroin and/or nanofibrous fibroin are functionalized with one or more bioactive agents selected from growth factors, drugs, antibiotics, antivirals, enzymes and vitamins.

3. The implantable medical device according to claim 1 for use for the containment of hernias and prolapses or as scaffold for the regeneration of tissues and organs of the peripheral nervous system, vascular system, cardiovascular system, central nervous system, skin and its layers, and containment and protection tissues of internal organs and tissues of the musculoskeletal system.

4. The implantable medical device according to claim 1, wherein the evaporation at a temperature between 10° C. and 100° C. of step e) is carried out under vacuum.

5. The implantable medical device of claim 1, wherein step b) of the process is carried out by force-spinning or electrospinning of a solution of fibroin in a solvent selected from formic acid, 1,1,1,3,3,3-hexafluoro-2-propanol, trifluoroacetic acid, ionic liquids, mixtures thereof, wherein said solvents are pure or in mixture with water, and wherein the concentration of fibroin is between 1% w/v and 30% w/v in case the solvent is formic acid, and between 5% w/v and 40% w/v in case one or more of said solvents different from formic acid are employed.

6. The implantable medical device of claim 5, wherein one or more bioactive agents selected from growth factors, drugs, cells, antibiotics, antivirals, enzymes and vitamins are added to said solution of fibroin.

7. The implantable medical device according to claim 6 for use for the containment of hernias and prolapses or as scaffold for the regeneration of tissues and organs of the peripheral nervous system, vascular system, cardiovascular system, central nervous system, skin and its layers, and containment and protection tissues of internal organs and tissues of the musculoskeletal system.

8. The implantable medical device according to claim 1, wherein said tissues and organs of the peripheral nervous system are peripheral nerves, said tissues and organs of the vascular system are veins, arteries and arteriovenous fistulas for vascular access, said tissues and organs of the cardiovascular system are coronary arteries and the heart muscle, said tissues and organs of the central nervous system are the spinal cord, said internal organs are dura mater, pericardium, pleura and peritoneum, and said tissues of the musculoskeletal system are tendons, ligaments and muscles.

9. The implantable medical device according to claim 4, wherein said tissues and organs of the peripheral nervous system are peripheral nerves, said tissues and organs of the vascular system are veins, arteries and arteriovenous fistulas for vascular access, said tissues and organs of the cardiovascular system are coronary arteries and the heart muscle, said tissues and organs of the central nervous system are the spinal cord, said internal organs are dura mater, pericardium, pleura and peritoneum, and said tissues of the musculoskeletal system are tendons, ligaments and muscles.

10. Implantable medical device comprising a hybrid structure comprising coupled microfibers and nanofibers of silk fibroin, having a mean separation force, measured according to the method defined in standard UNI EN ISO 13937-2:2000, of 53±11 cN when the microfiber part is in the form of crepe and of 21±9 cN when the microfiber part is in the form of organza.

11. The implantable medical device according to claim 1, in the shape of:
a tubular device with inner diameter of between 1 mm and 8 mm and wall thickness of between 0.2 mm and 4 mm;
a solid cylindrical device with outer diameter of between 2 mm and 15 mm; and
a planar device with thickness of between 0.05 mm and 5 mm.

12. The implantable medical device according to claim 10, in the shape of:
a tubular device with inner diameter of between 1 mm and 8 mm and wall thickness of between 0.2 mm and 4 mm;
a solid cylindrical device with outer diameter of between 2 mm and 15 mm; and
a planar device with thickness of between 0.05 mm and 5 mm.

* * * * *